(12) United States Patent
Selden et al.

(10) Patent No.: US 6,692,737 B1
(45) Date of Patent: *Feb. 17, 2004

(54) IN VIVO PROTEIN PRODUCTION AND DELIVERY SYSTEM FOR GENE THERAPY

(75) Inventors: Richard F Selden, Wellesley, MA (US); Douglas Treco, Arlington, MA (US); Michael W. Heartlein, Boxborough, MA (US)

(73) Assignee: Transkaryotic Therapies, Inc., Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/549,200

(22) Filed: Apr. 13, 2000

Related U.S. Application Data

(63) Continuation of application No. 08/443,936, filed on May 18, 1995, now Pat. No. 6,054,288, which is a division of application No. 08/334,797, filed on Nov. 4, 1994, now Pat. No. 6,048,729, which is a continuation of application No. 07/787,840, filed on Nov. 5, 1991, now abandoned.

(51) Int. Cl.$^7$ .................. A61K 48/00; C12N 15/09
(52) U.S. Cl. ............. 424/93.21; 424/93.1; 424/93.2; 514/44; 435/455
(58) Field of Search .............. 435/325; 424/93.21; 514/44; 800/3, 8, 9, 11, 13, 18

(56) References Cited

U.S. PATENT DOCUMENTS

| 4,396,601 A | 8/1983 | Salser et al. ............. 424/94.5 |
| 4,497,796 A | 2/1985 | Salser et al. ............. 424/94.5 |
| 4,789,550 A | 12/1988 | Hommel et al. ............ 424/493 |
| 4,892,538 A | 1/1990 | Aebischer et al. ....... 604/891.1 |
| 4,980,286 A | 12/1990 | Morgan et al. ............. 435/371 |
| 5,082,670 A | 1/1992 | Gage et al. ................ 424/520 |
| 5,089,397 A | 2/1992 | Kushner et al. .......... 435/69.1 |
| 5,166,059 A | 11/1992 | Pastan et al. ............. 435/69.7 |
| 5,175,255 A | 12/1992 | Thomason et al. ........ 530/380 |
| 5,194,596 A | 3/1993 | Tischer et al. ............. 530/399 |
| 5,219,740 A | 6/1993 | Miller et al. ............... 435/69.6 |

(List continued on next page.)

FOREIGN PATENT DOCUMENTS

| EP | 0038765 | 3/1981 |
| EP | 0236059 | 9/1987 |
| EP | 0255231 | 2/1988 |
| EP | 0289034 | 11/1988 |
| EP | 0452894 | 10/1991 |
| GB | 2159172 | 11/1985 |
| WO | WO 87/00201 | 1/1987 |
| WO | WO 89/05345 | 12/1987 |
| WO | WO 88/00239 | 1/1988 |
| WO | WO 89/07136 | 2/1988 |
| WO | WO 88/08306 | 3/1988 |
| WO | WO 90/06997 | 12/1988 |
| WO | WO 89/01517 | 2/1989 |
| WO | WO 90/12878 | 5/1989 |
| WO | WO 90/15863 | 6/1989 |
| WO | WO 90/06757 | 6/1990 |

(List continued on next page.)

OTHER PUBLICATIONS

Alberts, Molecular Biology of the Cell (Glossary), third edition, Garland Publishing, Inc., New York.

Antin et al., "Single Cell Analysis of Transfected Gene Expression in Primary Heart Cultures Containing Multiple Cell Types," BioTechniques 6:640–648, 1988.

Auchincloss et al., "Xenogeneic Transplantation," Annual Reviews in Immunology 16:433–470, 1998.

Barr et al., "Systemic Delivery of Recombinant Proteins by Genetically Modified Myoblasts," Science, 254:1507–1509, 1991.

Behr et al., "Efficient Gene Transfer Into Mammalian Primary Endocrine Cells with Lipopolyamine–coated DNA," Proceedings of the National Academy of Sciences U.S.A. 86:6982–6986, 1989.

Bennett et al., "A Role for Cyclosporin A in Gene Replacement Therapy," American Journal of Human Genetics 45:A109, 1989.

Bennett et al., "Suppression of Immunological Response Against a Novel Gene Product Delivered by Implants of Genetically Modified Fibroblasts," Molecular Biology and Medicine, 7:471–477, 1990.

Boggs, "Targeted Gene Modification for Gene Therapy of Stem Cells," International Journal of Cell Cloning 8:80–96, 1990.

(List continued on next page.)

*Primary Examiner*—Deborah Crouch
*Assistant Examiner*—Thaian N. Ton
(74) *Attorney, Agent, or Firm*—Clark & Elbing LLP

(57) ABSTRACT

The present invention relates to transfected primary and secondary somatic cells of vertebrate origin, particularly mammalian origin, transfected with exogenous genetic material (DNA) which encodes a desired (e.g., a therapeutic) product or is itself a desired (e.g., therapeutic) product, methods by which primary and secondary cells are transfected to include exogenous genetic material, methods of producing clonal cell strains or heterogenous cell strains, methods of gene therapy in which the transfected primary or secondary cells are used, and methods of producing antibodies using the transfected primary or secondary cells. The present invention includes primary and secondary somatic cells, such as fibroblasts, keratinocytes, epithelial cells, endothelial cells, glial cells, neural cells, formed elements of the blood, muscle cells, other somatic cells which can be cultured and somatic cell precursors, which have been transfected with exogenous DNA which is stably integrated into their genomes or is expressed in the cells episomally. The exogenous DNA either encodes a product, such as a translational product (e.g., a protein) or a transcriptional product (e.g., a ribozyme or an anti-sense nucleic acid sequence) which is a therapeutic product or is itself a therapeutic product (e.g., DNA which binds to a cellular regulatory protein or alters gene expression).

14 Claims, 10 Drawing Sheets

U.S. PATENT DOCUMENTS

| | | | |
|---|---|---|---|
| 5,272,071 A | 12/1993 | Chappel | 435/6 |
| 5,399,346 A | 3/1995 | Anderson et al. | 424/93.21 |
| 5,460,959 A | 10/1995 | Mulligan et al. | 435/456 |
| 5,789,215 A | 8/1998 | Berns et al. | 800/25 |
| 5,994,127 A | 11/1999 | Selden et al. | 435/325 |
| 6,048,524 A | 4/2000 | Selden et al. | 424/93.21 |
| 6,048,724 A | 4/2000 | Selden et al. | 435/325 |
| 6,048,729 A | 4/2000 | Selden et al. | 435/455 |
| 6,054,288 A * | 4/2000 | Selden et al. | 435/69.1 |
| 6,063,630 A | 5/2000 | Treco et al. | 435/463 |
| 6,187,305 B1 * | 2/2001 | Treco et al. | 424/93.21 |
| 6,214,622 B1 | 4/2001 | Treco et al. | 435/463 |

FOREIGN PATENT DOCUMENTS

| | | |
|---|---|---|
| WO | WO 90/11354 | 10/1990 |
| WO | WO 92/07573 | 10/1990 |
| WO | WO 92/12242 | 12/1990 |
| WO | WO 92/15676 | 3/1991 |
| WO | WO 91/06667 | 5/1991 |
| WO | WO 91/09955 | 7/1991 |
| WO | WO 91/13151 | 9/1991 |
| WO | WO 91/19796 | 12/1991 |
| WO | WO 92/03917 | 3/1992 |
| WO | WO 92/08796 | 3/1992 |
| WO | WO 92/19255 | 11/1992 |
| WO | WO 92/20808 | 11/1992 |
| WO | WO 93/04169 | 3/1993 |

OTHER PUBLICATIONS

Brash et al., "Strontium Phosphate Transfection of Human Cells in Primary Culture: Stable Expression of the Simian Virus 40 Large–T–Antigen Gene in Primary Human Bronchial Epithelial Cells," Molecular and Cellular Biology 7(5):2031–2034, 1987.

Brenner et al., "Expression of Collagen Genes in the Liver," Molecular Biology and Medicine 7:105–115, 1990.

Brigham et al., "Expression of a Prokaryotic Gene in Cultured Lung Endothelial Cells after Lipofection with a Plasmid Vector," Am. Journal of Respiratory Cell. and Molecular Biology 1:95–100, 1989.

Browne et al., "Erythropoietin: Gene Cloning, Protein Structure, and Biological Properties," Cold Spring Harbor Symposia on Quantitative Biology, vol. LI, Cold Spring Harbor Laboratory Press, Cold Spring Harbor, New York, p. 693–702, 1986.

Burrin et al., "Regulation of Transfected Glycoprotein Hormone α–Gene Expression in Primary Pituitary Cell Cultures," Molecular Endocrinology 3(10):1643–1651, 1989.

Camerini–Otero, "Right on Target," The New Biologist 2:337–341, 1990.

Cann et al., "High Efficiency Transfection of Primary Human Lymphocytes and Studies of Gene Expression," Oncogene 3:123–128, 1988.

Capecchi, "High Efficiency Transformation By Direct Microinjection of DNA Into Cultured Mammalian Cells," 22:479–488, 1980.

Capecchi, "Altering the Genome by Homologous Recombination," Science 244:1288–1292, 1989.

Chang et al., "High Efficiency Gene Transfection by Electroporation Using a Radio–Frequency Electric Field," Biochimica et Biophysica Acta, 1092:153–160, 1991.

Chang et al., "Autologous Fibroblast Implantation Feasibility and Potential Problems in Gene Replacement Therapy," Molecular Biology and Medicine, 7:461–470, 1990.

Cline, "Perspectives for Gene Therapy: Inserting New Genetic Information into Mammalian Cells by Physical Techniques and Viral Vectors," Pharmacology and Therapy 29:69–92, 1985.

Corey et al., "Erythropoiesis in Murine Long–Term Marrow Cultures Following Transfer of the Erythropoietin cDNA into Marrow Stromal Cells," Experimental Hematology, 18(3):201–204, 1990.

Crystal, "Transfer of Genes to Humans: Early Lessons and Obstacles to Success," Science 270:404–410, 1995.

Daubas et al., "Functional Activity of the Two Promoters of the Myosin Alkali Light Chain Gene in Primary Muscle Cell Cultures: Comparison with Other Muscle Gene Promoters and Other Culture Systems," Nucleic Acids Research 16(4):1251–1271, 1988.

Dhawan et al., "Systemic Delivery of Human Growth Hormone by Injection of Genetically Engineered Myoblasts," Science 254:1509–1512, 1991.

Diatloff–Zito et al., "Abnormal Response to DNA Crosslinking Agents of Fanconi Anemia Fibroblasts can be Corrected by Transfection with Normal Human DNA,"Proceedings of the National Academy of Sciences U.S.A. 83:7034–7038, 1986.

Doering et al., "Expression of a Novel Gene Product by Transplants of Genetically Modified Primary Fibroblasts in the Central Nervous Systems," Journal of Neuroscience Research 29:292–298, 1991.

Doetschmann et al., "Targeted Correction of a Mutant HPRT Gene in Mouse Embryonic Stem Cells," Nature, 330:576–578, 1987.

Doetschman et al., "Targeted Mutation of the HPRT Gene in Mouse Embryonic Stem Cells," Proceedings of the National Academy of Sciences U.S.A. 85:8583–8587, 1988.

Drucker, et al., "Cell–Specific Post–Translational Processing of Preproglucagon Expressed from a Metallothionein–Glucagon Fusion Gene," The Journal of Biological Chemistry 261(21):9637–9643, 1986.

Duncan et al., Biochemistry (Moscow) 62:1263–1274, 1997.

Faulds et al., "Epoetin (Recombinant Human Erythropoietin) A Review of Its Pharmacodynamic and Pharmacokinetic Properties and Therapeutic Potential in Anaemia and the Stimulation of Erythropoiesis," Drugs 38(6):863–899, 1989.

Finn et al., "Homologous Plasmid Recombination is Elevated in Immortally Transformed Cells," Molecular and Cellular Biology, 9:4009–4017, 1989.

Fishel et al., "Biochemical Studies of Homologous and Nonhomologous Recombination in Human Cells," Biochimie, 73:257–267, 1991.

Fountain et al., "Transfection of Primary Human Skin Fibroblasts by Electroporation," Gene 68(1):167–172, 1988.

Friedmann, "Progress Toward Human Gene Therapy," Science 244:1275–1281, 1989.

Frohman, "Cut, Paste, and Save: New Approaches to Altering Specific Gene in Mice," Cell 56:145–147, 1989.

Gao et al., "A Novel Cationic Liposome Reagent for Efficient Transfection of Mammalian Cells," Biochemical and Biophysical Research Communications 179(1):280–285, 1995.

Gareis et al., "Homologous Recombination of Exogenous DNA Fragments with Genomic DNA in Somatic Cells of Mice," Cellular and Molecular Biology 37(2):191–203, 1991.

Ginot et al., "Transfection of Hepatic Genes Into Adult Rat Hepatocytes in Primary Culture and Their Tissue–Specific Expression," European Journal of Biochemistry 180:289–294, 1989.

Glover, "Expression of Cloned Genes in Animal Cells," In "Gene Cloning, The Mechanics of DNA Manipulation," pp. 179–202, Chapman and Hall, New York, 1984.

Hammer et al., "Partial Correction of Murine Hereditary Growth Disorder by Germ–Line Incorporation of a New Gene," Nature 311:65–67, 1984.

Harper et al., "Expression of Transfected DNA by Primary Murine Keratinocytes," Journal of Investigative Dermatology 91(2):150–153, 1988.

Heartlein et al., "Long–Term Production and Delivery of Human Growth Hormone," Proceedings of the National Academy of Sciences U.S.A. 91:10967–10971, 1994.

Hesse et al., "Regulated Gene Expression in Transfected Primary Chicken Erythrocytes," Proceedings of the National Academy of Sciences U.S.A. 83:4312–4316, 1986.

Iannuzzi et al., "The Introduction of Biologically Active Foreign Genes into Human Respiratory Epithelial Cells Using Electroporation," Am. Rev. of Resp. Dis. 138:965–968, 1988.

Imagawa et al., "Regulatory Elements of the Erythropoietin Gene," Blood 77(2):278–285, 1991.

Itzhaki et al., "Targeted Disruption of a Human Interferon–Inducible Gene Detected by Secretion of Human Growth Hormone," Nucleic Acids Research 19(4):3835–3842, 1991.

Jensen et al., "High–Frequency Transfection of Cultured Human Epidermal Basal Cells That Differentiate to Form a Multilayered Tissue," Experimental Cell Research 189:163–168, 1990.

Joyner et al., "Production of a mutation in mouse En–2 gene by homologous recombination in embryonic stem cells," Nature 338:153–155, 1989.

Kaufman et al., "Strategies for Obtaining High Level Expression in Mammalian Cells," Technique 2:221–236, 1990.

Keating et al., "Gene Transfer by Electroporation: A Model for Gene Therapy," Progress in Clinical Biological Research 333:491–498, 1990.

Keating et al., "Effect of Different Promoters on Expression of Genes Introduced Into Hematopoietic and Marrow Stromal Cells by Electroporation," Experimental Hematology 18:99–102, 1990.

Kendrew, The Encyclopedia of Molecular Biology, Blackwell Science Ltd., Oxford, p. 1085, 1994.

Kramerova et al., "Expression of the Cloned Human Erythropoietin Gene in CHO Cells," Biopolim Kletka 5(2):47–51, 1989.

Kremer et al., "Regulation of Parathyroid Hormone–like Peptide in Cultured Normal Human Keratinocytes," The Journal of Clinical Investigation 87:884–893, 1991.

Kreymann et al., "Glucagon–Like Peptide–1 7–36: A Physiological Incretin In Man," The Lancet 2:1300–1304, 1987.

Kriegler, "Gene Transfer and Expression: A Laboratory Manual," Stockton Press, New York, 1990.

Le Mouellic et al., "Targeted Replacement of the Homeobox Gene Hox–3.1 by the *Escherichia coli lacZ* in Mouse Chimeric Embryos," Proceedings of the National Academy of Sciences U.S.A. 87:4712–4716, 1990.

Ledley, "Clinical Considerations in the Design of Protocols for Somatic Gene Therapy," Human Gene Therapy 2:77–83, 1991.

Lee et al., "Glucagon Gene 3'–Flanking Sequences Direct Formation of Proglucagon Messenger RNA 3'–Ends in Islet and Nonislet Cells Lines," Molecular Endocrinology, 4(6):800–806, 1990.

Lewin, Genes IV, Oxford University Press, Oxford, p. 820, 1990.

Litwer et al., "Reversion of the Maple Syrup Urine Disease Phenotype of Impaired Branched Chain Alpha–Ketoacid Dehydrogenase Complex Activity in Fibroblasts from an Affected Child," The Journal of Biological Chemistry 264:14597–14600, 1989.

Loeffler et al., "Lipopolyamine–Mediated Transfection Allows Gene Expression Studies in Primary Neuronal Cells," Journal of Neurochemistry 54:1812–1815, 1990.

Lu et al., "Gene Transfer by Lipofection in Rabbit and Human Secretory Epithelial Cells," Pflügers Archives 415:198–203, 1989.

Lupton et al., "Dominant Positive and Negative Selection Using A Hygromycin Phosphotransferase–Thymidine Kinase Fusion Gene," Molecular and Cellular Biology 11(6):3374–3378, 1991.

Mansour, "Gene Targeting in Murine Embryonic Stem Cells: Introduction of Specific Alterations into the Mammalian Genome," Genet. Anal. Tech Appl. 7:219–227, 1990.

Mansour et al., "Disruption of the Proto–Oncogene int–2 in Mouse Embryo–Derived Stem Cells: A General Strategy for Targeting Mutations to Non–Selectable Genes," Nature 336:348–352, 1988.

Marshall, "Gene Therapy's Growing Pains," Science 269:1050–1055, 1995.

Mercola et al., "Insertion of New Genetic Information into Bone Marrow Cells of Mice: Comparison of Two Selectable Genes," Annals New York Academy of Sciences, p. 272–280, 1982.

Mes–Masson et al., "Expression of Oncomodulin Does Not Lead to the Transformation or Immortalization of Mammalian Cells In Vitro," Journal of Cellular Science, 94:517–25, 1989.

Morgan et al., "Expression of an Exogeneous Growth Hormone Gene by Transplantable Human Epidermal Cells," Science 237:1476–1479, 1987.

Morgenstern et al., "Advanced Mammalian Gene Transfer: High Titre Retroviral Vectors With Multiple Drug Selection Markers and a Complementary Helper–Free Packaging Cell Line," Nucleic Acids Research 18(12):3587–3596, 1990.

Narayanan et al., "In Vivo Expression of a Nonselected Gene Transferred into Murine Hematopoietic Stem Cells by Electroporation," Biochemical and Biophysical Research Communications 141:1018–1024, 1986.

Ogura et al., "Implantation of Genetically Manipulated Fibroblasts into Mice as Antitumor α–Interferon Therapy," Cancer Research 50:5102–5106, 1990.

Orkin et al., "Report and Recommendations of the Panel to Assess the NIH Investment in Research on Gene Therapy," 1995.

Palmer et al., "Genetically Modified Skin Fibroblasts Persist Long After Transplantation But Gradually Inactivate Introduced Genes," Proceedings of the National Academy of Sciences U.S.A. 88:1330–1334, 1991.

Palmiter et al., "Metallothionein–Human GH Fusion Genes Stimulate Growth of Mice," Science 222:809–814, 1983.

Pasco et al., "Laboratory Methods, Efficient DNA–Mediated Gene Transfer into Primary Cultures of Adult Rat Hepatocytes," DNA 8(7):535–541, 1989.

Ponder et al., "Evaluation of Relative Promoter Strength in Primary Hepatocytes Using Optimized Lipofection," Human Gene Therapy 2:41–52, 1991.

Ponticelli et al., "Correction of Anaemia with Recombinant Human Erythropoietin," Nephron 52:201–208, 1989.

Potter, "Electroporation in Biology: Methods, Applications, and Instrumentation," Analytical Biochemistry 174:361–73, 1988.

Powell, "Human Erythropoietin Gene: High Level Expression In Stably Transfected Mammalian Cells and Chromosome Localization," Proceedings of the National Academy of Sciences U.S.A. 83:6465–6469, 1986.

Rippe et al., "DNA–Mediated Gene Transfer Into Adult Rat Hepatocytes in Primary Culture," Molecular and Cellular Biology 10(2):689–695, 1990.

Robertson, "Using Embryonic Stem Cells to Introduce Mutations into the Mouse Germ Line," Biology of Reproduction 44:238–245, 1991.

Rodriguez et al., "Recombinant DNA Techniques: An Introduction," The Benjamin/Cummings Publishing Company, Inc., London, 1983.

Rosenfeld et al., "In Vivo Transfer of the Human Cystic Fibrosis Transmembrane Conductance Regulator Gene to the Airway Epithelium," Cell 68:143–155, 1992.

Sambrook et al., "Molecular Cloning," Cold Spring Harbor Laboratory Press, Cold Spring Harbor, New York, p. 16.3–16.4, 1989.

Sandhu et al., "Human Gene Therapy," Critical Reviews in Biotechnology 17:307–326, 1997.

Scharfmann et al., "Long–Term In Vivo Expression of Retrovirus–Mediated Gene Transfer in Mouse Fibroblast Implants," Proceedings of the National Academy of Sciences U.S.A. 88:4626–4630, 1991.

Sedivy et al., "Positive Genetic Selection for Gene Disruption in Mammalian Cells by Homologous Recombination," Proceedings of the National Academy of Sciences U.S.A. 86:227–231, 1989.

Selden et al., "Regulation of Insulin–Gene Expression," The New England Journal of Medicine 317:1067–1076, 1987.

Selden et al., "Implantation of Genetically Engineered Fibroblasts into Mice: Implications for Gene Therapy," Science 236:714–718, 1987.

Shaham et al., "Transfection of Normal Human and Chinese Hamster DNA Corrects Diepoxybutane–induced Chromosomal Hypersensitivity of Fancomi Anemia Fibroblasts," Proceedings National Academy of Sciences U.S.A. 84:5853–5857, 1987.

Shesely et al., "Correction of a Human $\beta^s$–globin Gene by Gene Targeting," Proceedings of the National Academy of Sciences U.S.A. 88:4294–4298, 1991.

Sittler et al., "Tissue–Specific Expression of the Rat Growth Hormone Gene is Due to the Interaction of Multiple Promoter, Not Enhancer, Elements," DNA and Cell Biology 9(7):511–518, 1990.

Smith, "Regulation of Hematopoiesis," The Yale Journal of Biology and Medicine, 63(5):371–80, 1990.

Spandidos, "Electric Field–Mediated Gene Transfer (Electroporation) into Mouse Friend and Human K562 Erythroleukemic Cells," Gene Anal. Tech., 4:50–56, 1987.

Stacey et al., "Electroporation and DNA–Dependent Cell Death in Murine Macrophages," Immunology and Cell Biology 71:75–85, 1993.

St. Louis et al., "An Alternative Approach to Somatic Cell Gene Therapy," Proceedings of the National Academy of Sciences U.S.A., 85:3150–3154, 1988.

Tatsuka et al., "An Improved Method of Electroporation for Introducing Biologically Active Foreign Genes Into Cultured Mammalian Cells," Experimental Cell Research 178:154–162, 1988.

Thomas et al., "Site–Directed Mutagenesis by Gene Targeting in Mouse Embryo–Derived Stem Cells," Cell 51:503–512, 1987.

Thomas et al., "Targeted Disruption of the Murine int–1 Proto–oncogene Resulting in Severe Abnormalities in Midbrain and Cerebellar Development," Nature 346:847–850, 1990.

Thompson et al., "Germ Line Transmission and Expression of a Corrected HPRT Gene Produced by Gene Targeting in Embryonic Stem Cells," Cell 56:313–321, 1989.

Toneguzzo et al., "Stable Expression of Selectable Genes Introduced into Human Hematopoietic Stem Cells by Electric Field–Mediated DNA Transfer," Proceedings of the National Academy of Sciences U.S.A. 83:3496–3499, 1986.

Treco et al., "Non–Viral Gene Therapy," Molecular Medicine Today 1:314–321, 1995.

Treco et al., "Fibroblast Cell Biology and Gene Therapy," Somatic Gene Therapy, ISBN 0–8493–2440–8:49–60, 1995.

Tur–Kaspa et al., "Use of Electroporation to Introduce Biologically Active Foreign Genes Into Primary Rat Hepatocytes," Molecular and Cellular Biology 6:716–718, 1986.

Vega, "Prospects for Homologous Recombination in Human Gene Therapy," Human Genetics 87:245–253, 1991.

Verma, "Gene Therapy," Scientific American, 68–84, Nov., 1990.

Vogelstein et al., "The Multistep Nature of Cancer," Trends in Genetics 9(4):138–141, 1993.

Weatherall, "Scope and Limitations of Gene Therapy," British Medical Bulletin 51:1–11, 1995.

Weidle et al., "A New Expression System for Mammalian Cells Based on Putative Replicator Sequences of the Mouse and a Truncated Thymidine Kinase Gene," Gene 73:427–437, 1988.

Werner et al., "Expression of Transfected Genes by Differentiated, Postmitotic Neurons and Photoreceptors in Primary Cell Cultures," The Journal of Neuroscience Research 25:50–57, 1990.

Williams et al., "Introduction of New Genetic Material Into Pluripotent Haematopoietic Stem Cells of the Mouse," Nature 310:476–480 (1984).

Wolff et al., "Direct Gene Transfer Into Mouse Muscle In Vivo," Science 247:1465–1468, 1990.

Wu, "Receptor–Mediated Gene Delivery In Vivo," The Journal of Biological Chemistry 266(22):14338–14342, 1991.

Yang et al., "In Vivo and In Vitro Gene Transfer to Mammalian Somatic Cells by Particle Bombardment," Proceedings of the National Academy of Sciences U.S.A. 87:9568–9572, 1990.

Zheng et al. "Primary cells and established cell lines join DNA ends with the same efficiency relative to homologous recombination," Plasmid 22:99–105, 1989.

Zheng et al., "Fidelity of Targeted Recombination in Human Fibroblasts and Murine Embyronic Stem Cells," Proceedings of the National Academy of Sciences 88:8067–8071, 1991.

U.S. Ser. No. 09/328,130, filed Jun. 9, 1999.

U.S. Ser. No. 09/354,853, filed Jul. 16, 1999.
U.S. Ser. No. 09/374,669, filed Aug. 16, 1999.
U.S. Ser. No. 09/420,661, filed Oct. 19, 1999.
U.S. Ser. No. 09/431,821, filed Nov. 2, 1999.
U.S. Ser. No. 09/545,960, filed Apr. 10, 2000.
U.S. Ser. No. 09/549,697, filed Apr. 14, 2000.
U.S. Ser. No. 09/552,709, filed Apr. 19, 2000.

Selden et. al; Regulation of Insulin–Gene Expression, 1987, Seminars in Medicine of the Beth Israel Hospital vol. 317: 1067–1076.*

* cited by examiner

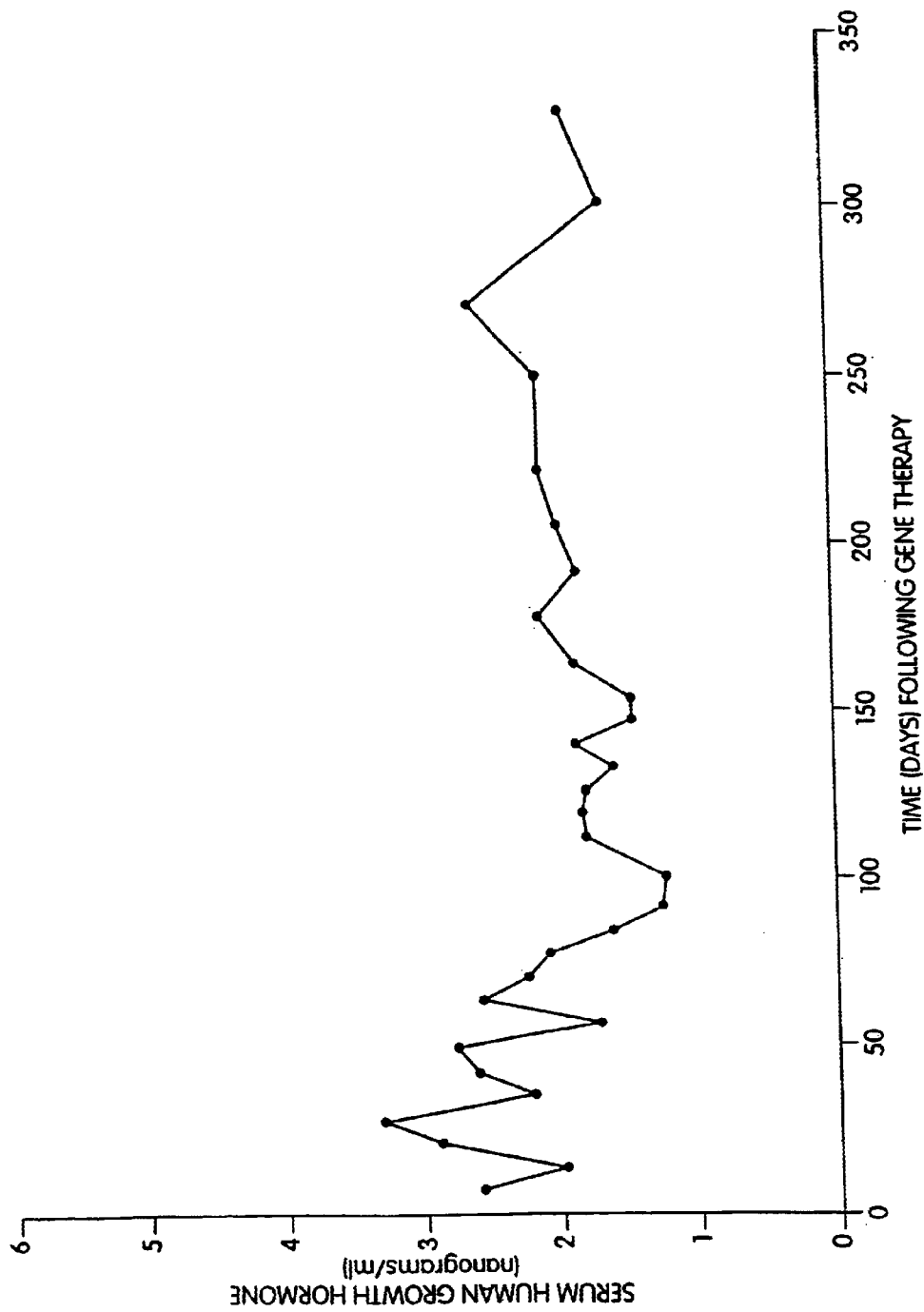

IN VIVO PROTEIN PRODUCTION AND DELIVERY SYSTEM FOR GENE THERAPY

This application is a continuation of, and claims priority from, U.S. Ser. No. 08/443,936, filed May 18, 1995 (now U.S. Pat. No. 6,054,288), which is a divisional of U.S. Ser. No. 08/334,797, filed Nov. 4, 1994 (now U.S. Pat. No. 6,048,729), which is a file wrapper continuation of U.S. Ser. No. 07/787,840, filed Nov. 5, 1991 (now abandoned).

BACKGROUND OF THE INVENTION

Efforts to develop human gene therapies have their roots in the 1950s, when early successes with kidney transplantation led to speculation that it might be possible to transplant cells from a normal individual into a patient suffering from a genetic disease. Soon after the discovery of the enzymatic defects in Gaucher's and Niemann-Pick disease, scientists considered organ and bone marrow transplantation and enzyme supplementation to treat rare genetic disorders (Brady, R., *NEJM* 275:312 (1966)). By the late 1960s and early 1970s, several investigators speculated that it also might be possible to introduce genes into a patient's own cells, and the cloning of the first human genes only a few years later intensified work in the field.

Until recently, almost all of the theoretical and experimental work on human gene therapy was centered on extremely rare genetic diseases, and gene therapy has come to mean, to many in the field, the modification of a patient's genes to treat a genetic disease. However, gene therapy has far wider applications than simply treatment of a genetic disease. Gene therapy is perhaps more appropriately described as medical intervention in which cells, either from the individual to be treated or another appropriate source, are modified genetically to treat or cure any condition, regardless of etiology, that will be ameliorated by the long-term delivery of a therapeutic protein. Gene therapy can therefore be thought of as an in vivo protein production and delivery system, and almost all diseases that are currently treated by the administration of proteins are candidates for treatment using gene therapy.

Gene therapy can be divided into two areas: germ cell and somatic cell gene therapy. Germ cell gene therapy refers to the modification of sperm cells, egg cells, zygotes, or early stage embryos. On the basis of both ethical and practical criteria, germ cell gene therapy is inappropriate for human use. In contrast to germ cell gene therapy, somatic cell gene therapy would affect only the person under treatment (somatic cells are cells that are not capable of developing into whole individuals and include all of the body's cells with the exception of the germ cells). As such, somatic cell gene therapy is a reasonable approach to the treatment and cure of certain disorders in human beings.

In a somatic cell gene therapy system, somatic cells (e.g., fibroblasts, hepatocytes, or endothelial cells) are removed from the patient, cultured in vitro, transfected with the gene(s) of therapeutic interest, characterized, and reintroduced into the patient. The means by which these five steps are carried out are the distinguishing features of a given gene therapy system.

Presently-available approaches to gene therapy make use of infectious vectors, such as retroviral vectors, which include the genetic material to be expressed. Such approaches have limitations, such as the potential of generating replication-competent virus during vector production; recombination between the therapeutic virus and endogenous retroviral genomes, potentially generating infectious agents with novel cell specificities, host ranges, or increased virulence and cytotoxicity; independent integration into large numbers of cells, increasing the risk of a tumorigenic insertional event; limited cloning capacity in the retrovirus (which restricts therapeutic applicability) and short-lived in vivo expression of the product of interest. A better approach to providing gene products, particularly one which avoids the risks associated with presently-available methods and provides long-term production, would be valuable.

SUMMARY OF THE INVENTION

The present invention relates to transfected primary and secondary somatic cells of vertebrate origin, particularly mammalian origin, transfected with exogenous genetic material (DNA) which encodes a desired (e.g., a therapeutic) product or is itself a desired (e.g., therapeutic) product, methods by which primary and secondary cells are transfected to include exogenous genetic material, methods of producing clonal cell strains or heterogenous cell strains, methods of gene therapy in which the transfected primary or secondary cells are used, and methods of producing antibodies using the transfected primary or secondary cells.

As used herein, the term primary cell includes cells present in a suspension of cells isolated from a vertebrate tissue source (prior to their being plated i.e., attached to a tissue culture substrate such as a dish or flask), cells present in an explant derived from tissue, both of the previous types of cells plated for the first time, and cell suspensions derived from these plated cells. The term secondary cell or cell strain refers to cells at all subsequent steps in culturing. That is, the first time a plated primary cell is removed from the culture substrate and replated (passaged), it is referred to herein as a secondary cell, as are all cells in subsequent passages. Secondary cells are cell strains which consist of secondary cells which have been passaged one or more times. A cell strain consists of secondary cells that: 1) have been passaged one or more times; 2) exhibit a finite number of mean population doublings in culture; 3) exhibit the properties of contact-inhibited, anchorage dependent growth (anchorage-dependence does not apply to cells that are propagated in suspension culture); and 4) are not immortalized. A "clonal cell strain" is defined as a cell strain that is derived from a single founder cell. A "heterogenous cell strain" is defined as a cell strain that is derived from two or more founder cells.

The present invention includes primary and secondary somatic cells, such as fibroblasts, keratinocytes, epithelial cells, endothelial cells, glial cells, neural cells, formed elements of the blood, muscle cells, other somatic cells which can be cultured and somatic cell precursors, which have been transfected with exogenous DNA which is stably integrated into their genomes or is expressed in the cells episomally. The resulting cells are referred to, respectively, as transfected primary cells and transfected secondary cells. The exogenous DNA either encodes a product, such as a translational product (e.g., a protein) or a transcriptional product (e.g., a ribozyme or an anti-sense nucleic acid sequence) which is a therapeutic product or is itself a therapeutic product (e.g., DNA which binds to a cellular regulatory protein or alters gene expression). In the embodiment in which the exogenous DNA encodes a translational or transcriptional product to be expressed by the recipient cells, the resulting product is retained within the cell, incorporated into the cell membrane or secreted from the cell. In this embodiment, the exogenous DNA encoding the therapeutic product is introduced into cells along with additional DNA sequences sufficient for expression of the exogenous DNA in transfected cells and is operatively linked to those sequences. In the embodiment in which the exogenous DNA is not expressed, there is no gene product and the DNA itself is the therapeutic product. In this embodiment, exogenous DNA is, for example, DNA sequences which bind to a cellular regulatory protein, DNA sequences sufficient for sequestration of a protein or nucleic acid present in the transfected primary or secondary cell, DNA sequences which alter secondary or tertiary chromosomal structure or DNA sequences which are transcriptional regulatory elements. Such primary cells modified to express or render available exogenous DNA are referred to herein as transfected primary cells, which include cells removed from tissue and placed on culture medium for the first time. Secondary cells modified to express or render available exogenous DNA are referred to herein as transfected secondary cells.

Primary and secondary cells transfected by the subject method can be seen to fall into three types or categories: 1) cells which do not, as obtained, make or contain the therapeutic product, 2) cells which make or contain the therapeutic product but in lower quantities than normal (in quantities less than the physiologically normal lower level) or in defective form, and 3) cells which make the therapeutic product at physiologically normal levels, but are to be augmented or enhanced in their content or production.

Exogenous DNA is introduced into primary or secondary cells by a variety of techniques. For example, a construct which includes exogenous DNA encoding a therapeutic protein and additional DNA sequences necessary for expression in recipient cells is introduced into primary or secondary cells by electroporation, microinjection, or other means (e.g., calcium phosphate precipitation, modified calcium phosphate precipitation, polybrene precipitation, liposome fusion, receptor-mediated DNA delivery). Alternatively, a vector, such as a retroviral vector, which includes exogenous DNA can be used and cells can be genetically modified as a result of infection with the vector.

In addition to the exogenous DNA, transfected primary and secondary cells may optionally contain DNA encoding a selectable marker, which is expressed and confers upon recipients a selectable phenotype, such as antibiotic resistance, resistance to a cytotoxic agent, nutritional prototrophy or expression of a surface protein. Its presence makes it possible to identify and select cells containing the exogenous DNA. A variety of selectable marker genes can be used, such as neo, gpt, dhfr, ada, pac, hyg, mdr and hisD.

Transfected cells of the present invention are useful, as populations of transfected primary cells, transfected clonal cell strains, transfected heterogenous cell strains, and as cell mixtures in which at least one representative cell of one of the three preceding categories of transfected cells is present, as a delivery system for treating an individual with an abnormal or undesirable condition which responds to delivery of a therapeutic product, which is either: 1) a therapeutic protein (e.g., a protein which is absent, underproduced relative to the individual's physiologic needs, defective or inefficiently or inappropriately utilized in the individual; a protein with novel functions, such as enzymatic or transport functions) or 2) a therapeutic nucleic acid (e.g., DNA which binds to or sequesters a regulatory protein, RNA which inhibits gene expression or has intrinsic enzymatic activity). In the method of the present invention of providing a therapeutic protein or nucleic acid, transfected primary cells, clonal cell strains or heterogenous cell strains, are administered to an individual in whom the abnormal or undesirable condition is to be treated or prevented, in sufficient quantity and by an appropriate route, to express or make available the exogenous DNA at physiologically relevant levels. A physiologically relevant level is one which either approximates the level at which the product is produced in the body or results in improvement of the abnormal or undesirable condition.

Clonal cell strains of transfected secondary cells (referred to as transfected clonal cell strains) expressing exogenous DNA (and, optionally, including a selectable marker gene) are produced by the method of the present invention. The present method includes the steps of: 1) providing a population of primary cells, obtained from the individual to whom the transfected primary cells will be administered or from another source; 2) introducing into the primary cells or into secondary cells derived from primary cells a DNA construct which includes exogenous DNA as described above and the necessary additional DNA sequences described above, producing transfected primary or secondary cells; 3) maintaining transfected primary or secondary cells under conditions appropriate for their propagation; 4) identifying a transfected primary or secondary cell; and 5) producing a colony from the transfected primary or secondary cell identified in (4) by maintaining it under appropriate culture conditions and for sufficient time for its propagation, thereby producing a cell strain derived from the (founder) cell identified in (4). In one embodiment of the method, exogenous DNA is introduced into genomic DNA by homologous recombination between DNA sequences present in the DNA construct and genomic DNA.

In one embodiment of the present method of producing a clonal population of transfected secondary cells, a cell suspension containing primary or secondary cells is combined with exogenous DNA encoding a therapeutic product and DNA encoding a selectable marker, such as the neo gene. The two DNA sequences are present on the same. DNA construct or on two separate DNA constructs. The resulting combination is subjected to electroporation, generally at 250–300 volts with a capacitance of 960 $\mu$Farads and an appropriate time constant (e.g., 14 to 20 m sec) for cells to take up the DNA construct. In an alternative embodiment, microinjection is used to introduce the DNA construct into primary or secondary cells. In either embodiment, introduction of the exogenous DNA results in production of transfected primary or secondary cells.

In the method of producing heterogenous cell strains of the present invention, the same steps are carried out as described for production of a clonal cell strain, except that a single transfected primary or secondary cell is not isolated and used as the founder cell. Instead, two or more transfected primary or secondary cells are cultured to produce a heterogenous cell strain.

The subject invention also relates to a method of producing antibodies specific for the protein encoded by the exogenous DNA. In the method, transfected primary or secondary cells expressing an antigen against which antibodies are desired are introduced into an animal recipient (e.g., rabbit, mouse, pig, dog, cat, goat, guinea pig, sheep, non-human primate). The animal recipient produces antibodies against the antigen expressed, which may be an entire protein antigen or a peptide encoded by a fragment of the intact gene which encodes the entire antigen. Polyclonal sera is obtained from the animals. It is also possible to produce monoclonal antibodies through the use of transfected primary or secondary cells. Splenocytes are removed from an animal recipient of transfected primary or secondary cells expressing the antigen against which monoclonal antibodies are desired. The splenocytes are fused with myeloma cells, using known methods, such as that of Koprowski et al. (U.S.

Pat. No. 4,172,124) or Kohler et al., (*Nature* 256:495–497 (1975)) to produce hybridoma cells which produce the desired monoclonal antibody. The polyclonal antisera and monoclonal antibodies produced can be used for the same purposes (e.g., diagnostic, preventive, therapeutic purposes) as antibodies produced by other methods.

The present invention has wide applicability in treating abnormal or undesired conditions and can be used to provide a variety of products to an individual. For example, it can be used to provide secreted proteins (with either predominantly systemic or predominantly local effects), membrane proteins (e.g., for imparting new or enhanced cellular responsiveness, facilitating removal of a toxic product or marking or targeting a cell) or intracellular proteins (e.g., for affecting gene expression or producing autolytic effects). In addition, it can be used to provide engineered DNA which binds or sequesters a cellular protein, to produce engineered RNA useful in an anti-sense approach to altering gene expression or to provide antigens against which immune response occurs in an individual (to prevent disease as by vaccination or to suppress an existing condition).

The present invention is particularly advantageous in treating abnormal or undesired conditions in that it: 1) is curative (one gene therapy treatment has the potential to last a patient's lifetime); 2) allows precise dosing (the patient's cells continuously determine and deliver the optimal dose of the required protein based on physiologic demands, and the stably transfected cell strains can be characterized extensively in vitro prior to implantation, leading to accurate predictions of long term function in vivo); 3) is simple to apply in treating patients; 4) eliminates issues concerning patient compliance (following a one-time gene therapy treatment, daily protein injections are no longer necessary); 5) reduces treatment costs (since the therapeutic protein is synthesized by the patient's own cells, investment in costly protein production and purification is unnecessary); and 6) is safe (the invention does not use infectious agents such as retroviruses to genetically engineer the patient's cells, thereby overcoming the safety and efficacy issues that have hampered other gene therapy systems).

BRIEF DESCRIPTION OF THE DRAWINGS

FIG. 7 is a graphic representation of serum hGH levels over time in mice in which $3 \times 10^6$ cells were implanted under the renal capsule.

FIG. 8A, from mice having 5-week-old implants and FIG. 8B, from mice having 10-week-old implants.

DETAILED DESCRIPTION OF THE INVENTION

Figure 1:
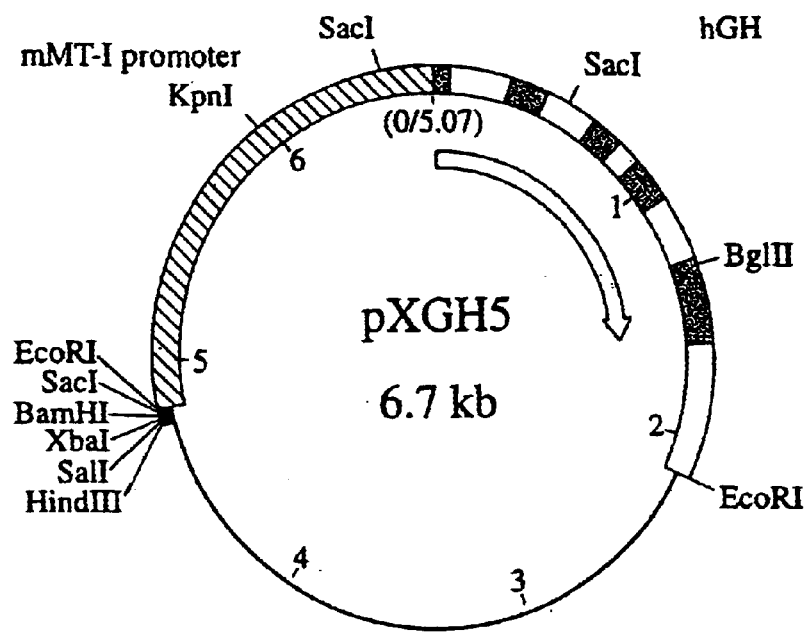
FIG. 1 is a schematic representation of plasmid pXGH5, which includes the human growth hormone (hGH) gene under the control of the mouse metallothionein promoter.

As described herein, primary or secondary cells of vertebrate, particularly mammalian, origin have been transfected with exogenous DNA encoding a therapeutic product and shown to produce the encoded therapeutic protein stably and reproducibly, both in vitro and in vivo, over extended periods of time. In addition, the transfected primary and secondary cells have been shown to express the encoded product in vivo at physiologically relevant levels, to be recoverable after implantation and, upon reculturing, to grow and display their preimplantation properties. This demonstration is in sharp contrast to what one of skill in the art would predict, since, for example, even experts in the field see the finite life span of normal somatic cells and the inability to isolate or grow the relevant transplantable cells as precluding their use for gene therapy unless the cells are genetically modified using retroviruses. Miller, A. D., *Blood*, 76:271–278 (1990). However, the transplantation of retrovirally-treated fibroblasts has been shown to provide, at best, only transient metabolic improvements, and is seen to have serious limitations as a therapeutic system. Normal (non immortal) fibroblasts are characterized as being "much more difficult to transfect than continuous cell lines by using calcium phosphate precipitation techniques." Miller, A. D., *Blood*, 76:271–278 (1990). Furthermore, in considering non-retroviral techniques for gene therapy, it is typical of experts in the field to believe ". . . the efficiency of gene delivery is dismal . . . A physician would have to obtain an impossible number of cells from patients to guarantee the appropriate alteration of the millions required for therapy." (Verma, I. M. *Scient. Amer.* November 1990, pages 68–84).

Surprisingly, Applicants have been able to produce transfected primary and secondary cells which include exogenous DNA encoding a desired product, (i.e., a translation product which is a therapeutic protein or an antigen against which antibodies are produced) and stably express the exogenous DNA. It is also possible, using the method described herein, to produce transfected primary and secondary cells which include exogenous DNA encoding other translation products (novel proteins not made in nature) or transcription products (e.g., anti-sense RNA or ribozymes) or exogenous DNA which itself is a therapeutic product (e.g., exogenous DNA which binds a regulatory protein present in the transfected cell).

The transfected primary or secondary cells may also include DNA encoding a selectable marker which confers a selectable phenotype upon them, facilitating their identification and isolation. Applicants have also developed methods for producing transfected primary or secondary cells which stably express exogenous DNA, clonal cell strains and heterogenous cell strains of such transfected cells, methods of producing the clonal and heterogenous cell strains, and methods of treating or preventing an abnormal or undesirable condition through the use of populations of transfected primary or secondary cells of the present invention.

Transfected Cells

Primary and secondary cells to be transfected by the present method can be obtained from a variety of tissues and include all cell types which can be maintained and propagated in culture. For example, primary and secondary cells which can be transfected by the present method include fibroblasts, keratinocytes, epithelial cells (e.g., mammary epithelial cells, intestinal epithelial cells), endothelial cells, glial cells, neural cells, formed elements of the blood (e.g., lymphocytes, bone marrow cells), muscle cells and precursors of these somatic cell types. Primary cells are preferably obtained from the individual to whom the transfected primary or secondary cells are administered. However, primary cells may be obtained from a donor (other than the recipient) of the same species or another species (e.g., mouse, rat, rabbit, cat, dog, pig, cow, bird, sheep, goat, horse).

Transfected primary and secondary cells have been produced, with or without phenotypic selection, as described in Examples 4–6, and shown to express exogenous DNA encoding a therapeutic product.

Exogenous DNA

Exogenous DNA incorporated into primary or secondary cells by the present method is: 1) DNA which encodes a translation or transcription product, such as a translation or transcription product useful to treat an existing condition or prevent it from occurring and 2) DNA which does not encode a gene product but is itself useful, such as DNA useful to treat an existing condition or prevent it from occurring.

DNA incorporated into primary or secondary cells can be an entire gene encoding an entire desired product or a gene portion which encodes, for example, the active or functional protion(s) of the product. The product can be, for example, a hormone, a cytokine, an antigen, an antibody, an enzyme, a clotting factor, a transport protein, a receptor, a regulatory protein, a structural protein, an anti-sense RNA, a ribozyme or a protein or a nucleic acid which does not occur in nature. The DNA can be obtained from a source in which it occurs in nature or can be produced, using genetic engineering techniques or synthetic processes. The DNA transfected into primary or secondary cells can encode one or more therapeutic products. After transfection into primary or secondary cells, the exogenous DNA is stably incorporated into the recipient cell's genome (along with the additional sequences present in the DNA construct used), from which it is expressed or otherwise functions. Alternatively, the exogenous DNA may exist episomally within the transfected primary or secondary cells.

Selectable Markers

A variety of selectable markers can be incorporated into primary or secondary cells. For example, a selectable marker which confers a selectable phenotype such as drug resistance, nutritional auxotrophy, resistance to a cytotoxic agent or expression of a surface protein, can be used. Selectable marker genes which can be used include neo, gpt, dhfr, ada, pac, hyg and hisd. The selectable phenotype conferred makes it possible to identify and isolate recipient primary or secondary cells.

DNA Constructs

DNA constructs, which include exogenous DNA and, optionally, DNA encoding a selectable marker, along with additional sequences necessary for expression of the exogenous DNA in recipient primary or secondary cells, are used to transfect primary or secondary cells in which the encoded product is to be produced. DNA constructs which include exogenous DNA sequences which do not encode a gene product (and are the therapeutic product) and, optionally, include DNA encoding a selectable marker, can be used to transfect primary and secondary cells. Alternatively, infectious vectors, such as retroviral, herpes, adenovirus, adenovirus-associated, mumps and poliovirus vectors, can be used for this purpose.

A DNA construct which includes the exogenous DNA and additional sequences, such as sequences necessary for expression of the exogenous DNA, can be used (e.g., plasmid p XGH5). Optionally, the DNA construct may include a bacterial origin of replication and bacterial antibiotic resistance markers, which allow for large-scale plasmid propagation in bacteria. A DNA construct which includes DNA encoding a selectable marker, along with additional sequences, such as a promoter, poly-adenylation site and splice junctions, can be used to confer a selectable phenotype upon transfected primary or secondary cells (e.g., plasmid pcDNEO). The two DNA constructs are co-transfected into primary or secondary cells, using methods described herein. Alternatively, one DNA construct which includes exogenous DNA, a selectable marker gene and additional sequences (e.g., those necessary for expression of the exogenous DNA and for expression of the selectable marker gene) can be used. Such a DNA construct (pXGH301) is described in FIG. 3; it includes the hGH gene and the neo gene.

Figure 4:
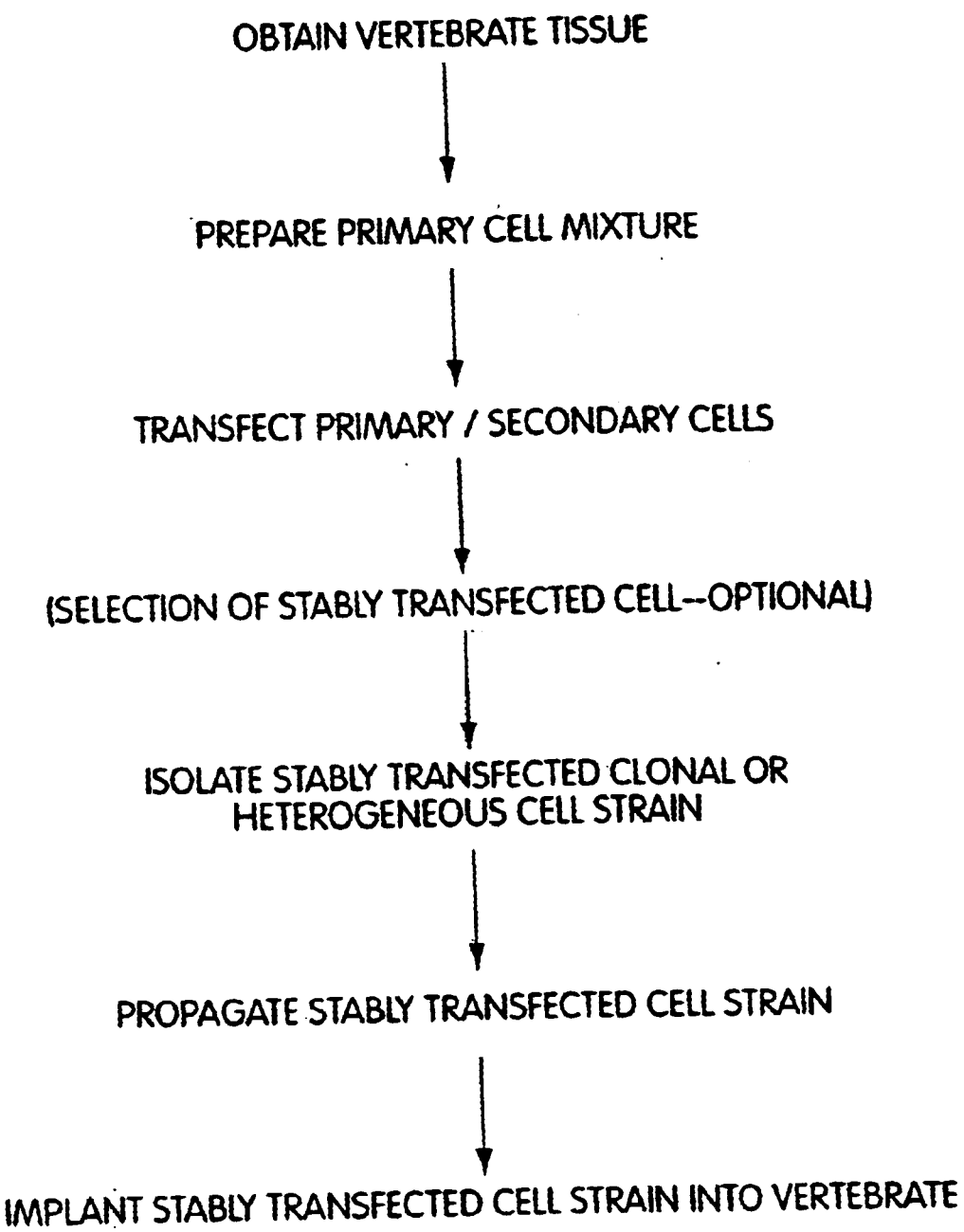
FIG. 4 is a flow chart of the method of the present invention.

Transfection of Primary or Secondary Cells and Production of Clonal or Heterogenous Cell Strains The method of the present invention is represented schematically in FIG. 4, As shown, vertebrate tissue is first obtained; this is carried out using known procedures, such as punch biopsy or other surgical methods of obtaining a tissue source of the primary cell type of interest. For example, punch biopsy is used to obtain skin as a source of fibroblasts or keratinocytes. A mixture of primary cells is obtained from the tissue, using known methods, such as enzymatic digestion or explanting. If enzymatic digestion is used, enzymes such as collagenase, hyaluronidase, dispase, pronase, trypsin, elastase and chymotrypsin can be used.

Figure 2:
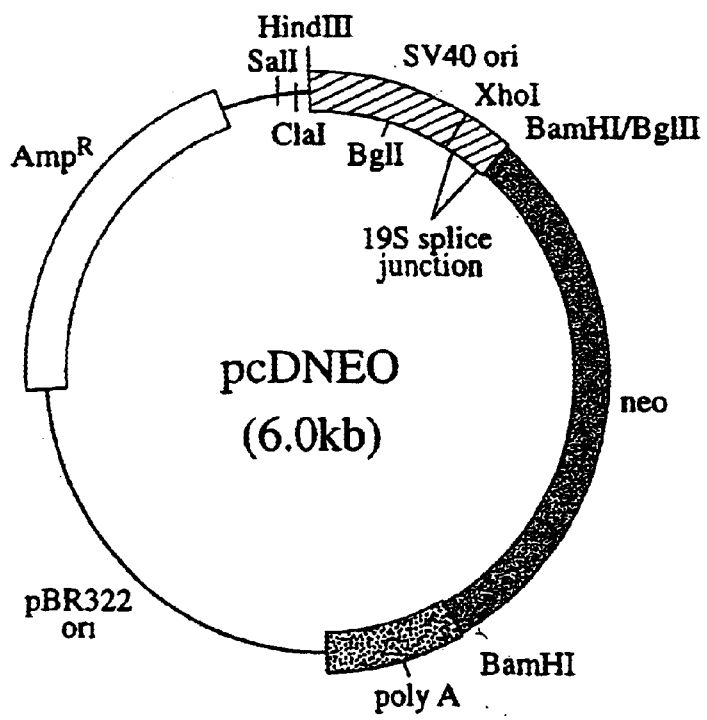
FIG. 2 is a schematic representation of plasmid pcDNEO, which includes the neo coding region (BamHI-BglII fragment) from plasmid pSV2neo inserted into the BamHI site of plasmid pcD; the Amp-R and pBR322ori sequences from pBR322; and the polyA, 16S splice junctions and early promoter regions from SV40.

The resulting primary cell mixture can be transfected directly or it can be cultured first, removed from the culture plate and resuspended before transfection is carried out. Primary cells or secondary cells are combined with exogenous DNA to be stably integrated into their genomes and, optionally, DNA encoding a selectable marker, and treated in order to accomplish transfection. The exogenous DNA and selectable marker-encoding DNA are each on a separate construct (e.g., pXGH5 and pcDNEO, see FIGS. 1 and 2) or on a single construct (e.g., pXGH301, see FIG. 3) and an appropriate quantity of DNA to ensure that at least one stably transfected cell containing and appropriately expressing exogenous DNA is produced. In general, 0.1 to 500 μg DNA is used.

Using the present methods to introduce only a selectable marker gene, between 170 (1 in 588 starting cells treated by electroporation, Example 4) and 2000 (1 in 49 starting cells treated by microinjection, Example 6) stably transfected cells are generated per 100,000 starting cells. Using the present methods to introduce a therapeutic gene as well as a selectable marker gene, between 7 (1 in 14,705 starting cells treated by electroporation, Example 4) and 950 (1 in 105 starting cells treated by microinjection, Example 6) stably transfected cells are generated per 100,000 starting cells. Of these stable transfectants, from 43 to 90% express the gene of therapeutic interest. Since only a single appropriately expressing cell is required, it is clearly possible to use substantially fewer starting cells. Conversely, using transfection techniques which are substantially less efficient than the present methods, it would not be possible to obtain even a single such cell unless large amount of the individual's tissue is used as the source of starting cells.

In one embodiment of the present method of producing transfected primary or secondary cells, transfection is effected by electroporation, as described in the Examples. Electroporation is carried out at appropriate voltage and capacitance (and corresponding time constant) to result in entry of the DNA construct(s) into the primary or secondary cells. Electroporation can be carried out over a wide range of voltages (e.g., 50 to 2000 volts) and corresponding capacitance. As described herein, electroporation is very efficient if carried out at an electroporation voltage in the range of 250–300 volts and a capacitance of 960 $\mu$Farads (see Examples 1, 4, 5 and 6). Total DNA of approximately 0.1 to 500 $\mu$g is generally used. As described in the Examples, total DNA of 60 pg and voltage of 250–300 volts with capacitance of 960 $\mu$Farads for a time constant 14–20 of msec. has been used and shown to be efficient.

In another embodiment of the present method, primary or secondary cells are transfected using microinjection. See, for instance, Example 6. Alternatively, known methods such as calcium phosphate precipitation, modified calcium phosphate precipitation and polybrene precipitation, liposome fusion and receptor-mediated gene delivery can be used to transfect cells. A stably, transfected cell is isolated and cultured and subcultivated, under culturing conditions and for sufficient time, to propagate the stably transfected secondary cells and produce a clonal cell strain of transfected secondary cells. Alternatively, more than one transfected cell is cultured and subculturated, resulting in production of a heterogenous cell strain.

Transfected primary or secondary cells undergo a sufficient number of doublings to produce either a clonal cell strain or a heterogenous cell strain of sufficient size to provide the therapeutic product to an individual in effective amounts. In general, for example, 0.1 cm$^2$ of skin is biopsied and assumed to contain 100,000 cells; one cell is used to produce a clonal cell strain and undergoes approximately 27 doublings to produce 100 million transfected secondary cells. If a heterogenous cell strain is to be produced from an original transfected population of approximately 100,000 cells, only 10 doublings are needed to produce 100 million transfected cells.

The number of required cells in a transfected clonal or heterogenous cell strain is variable and depends on a variety of factors, including but not limited to, the use of the transfected cells, the functional level of the exogenous DNA in the transfected cells, the site of implantation of the transfected cells (for example, the number of cells that can be used is limited by the anatomical site of implantation), and the age, surface area, and clinical condition of the patient. To put these factors in perspective, to deliver therapeutic levels of human growth hormone in an otherwise healthy 10 kg patient with isolated growth hormone deficiency, approximately one to five hundred million transfected fibroblasts would be necessary (the volume of these cells is about that of the very tip of the patient's thumb).

Episomal Expression of Exogenous DNA

DNA sequences that are present within the cell yet do not integrate into the genome are referred to as episomes. Recombinant episomes may be useful in at least three settings: 1) if a given cell type is incapable of stably integrating the exogenous DNA; 2) if a given cell type is adversely affected by the integration of DNA; and 3) if a given cell type is capable of improved therapeutic function with an episomal rather than integrated DNA.

Using the transfection and culturing approaches to gene therapy described in Examples 1, 2, 4, 5, and 6, exogenous DNA in the form of episomes can be introduced into vertebrate primary and secondary cells. Plasmid pXGH301 can be converted into such an episome by the addition DNA sequences for the Epstein-Barr virus origin of replication and nuclear antigen [Yates, J. L. *Nature* 319:780–7883 (1985)]. Alternatively, vertebrate autonomously replicating sequences can be introduced into the construct (Weidle, U. H. Gene 73(2):427–437 (1988). These and other episomally derived sequences can also be included in DNA constructs without selectable markers, such as pXGH5. The episomal exogenous DNA is then introduced into primary or secondary vertebrate cells as described in this application (if a selective marker is included in the episome a selective agent is used to treat the transfected cells).

Implantation of Clonal Cell Strain or Heterogenous Cell Strain of Transfected Secondary Cells The transfected cells produced as described above are introduced into an individual to whom the therapeutic product is to be delivered, using known methods. The clonal cell strain or heterogenous cell strain is then introduced into an individual, using known methods, using various routes of administration and at various sites (e.g., renal subcapsular, subcutaneous, central nervous system (including intrathecal), intravascular, intrahepatic, intrasplanchnic, intraperitoneal (including intraomental), or intramuscular implantation). Once implanted in the individual, the transfected cells produce the therapeutic product encoded by the exogenous DNA or are affected by the exogenous DNA itself. For example, an individual who has been diagnosed with Hemophilia B, a bleeding disorder that is caused by a deficiency in Factor IX, a protein normally found in the blood, is a candidate for a gene therapy cure. The patient has a small skin biopsy performed; this is a simple procedure which can be performed on an out-patient basis. The piece of skin, approximately the size of a matchhead, is taken, for example, from under the arm and requires about one minute to remove. The sample is processed, resulting in isolation of the patient's cells (in this case, fibroblasts) and genetically engineered to produce the missing Factor IX. Based on the age, weight, and clinical condition of the patient, the required number of cells are grown in large-scale culture. The entire process usually requires 4–6 weeks and, at the end of that time, the appropriate number of genetically-engineered cells are introduced into the individual, once again as an out-patient (e.g., by injecting them back under the patient's skin). The patient is now capable of producing his or her own Factor IX and is no longer a hemophiliac.

A similar approach can be used to treat other conditions or diseases. For example, short stature can be treated by administering human growth hormone to an individual by implanting primary or secondary cells which express human growth hormone.

As this example suggests, the cells used will generally be patient-specific genetically-engineered cells. It is possible, however, to obtain cells from another individual of the same species or from a different species. Use of such cells might require administration of an immunosuppressant, alteration of histo-compatibility antigens, or use of a barrier device to prevent rejection of the implanted cells. For many diseases, this will be a one-time treatment and, for others, multiple gene therapy treatments will be required.

Uses of Transfected Primary and Secondary Cells and Cell Strains

Transfected primary or secondary cells or cell strains have wide applicability as a vehicle or delivery system for therapeutic products, such as enzymes, hormones, cytokines, antigens, antibodies, clotting factors, anti-sense RNA, regulatory proteins, transcription proteins, receptors, structural proteins, ribozymes, novel (non-naturally occurring) proteins and nucleic acid products, and engineered DNA. For example, transfected primary or secondary cells can be used to supply a therapeutic protein, including, but not limited to, Factor VIII, Factor IX, erythropoietin, alpha-1 antitrypsin, calcitonin, glucocerebrosidase, growth hormone, low density lipoprotein (LDL), receptor IL-2 receptor and its antagonists, insulin, globin, immunoglobulins, catalytic antibodies, the interleukins, insulin-like growth factors, superoxide dismutase, immune responder modifiers, parathyroid hormone and interferon, nerve growth factors, tissue plasminogen activators, and colony stimulating factors. Alternatively, transfected primary and secondary cells can be used to immunize an individual (i.e., as a vaccine).

The wide variety of uses of cell strains of the present invention can perhaps most conveniently be summarized as shown below. The cell strains can be used to deliver the following therapeutic products.

1. a secreted protein with predominantly systemic effects;
2. a secreted protein with predominantly local effects;
3. a membrane protein imparting new or enhanced cellular responsiveness;
4. membrane protein facilitating removal of a toxic product;
5. a membrane protein marking or targeting a cell;
6. an intracellular protein;
7. an intracellular protein directly affecting gene expression;
8. an intracellular protein with autolytic effects;
9. gene product-engineered DNA which binds to or sequesters a regulatory protein;
10. a ribozyme; and
11. antisense-engineered RNA to inhibit gene expression.

The transfected primary or secondary cells of the present invention can be used to administer therapeutic proteins (e.g., hormones, enzymes, clotting factors) which are presently administered intravenously, intramuscularly or subcutaneously, which requires patient cooperation and, often, medical staff participation. When transfected primary or secondary cells are used, there is no need for extensive purification of the polypeptide before it is administered to an individual, as is generally necessary with an isolated polypeptide. In addition, transfected primary or secondary cells of the present invention produce the therapeutic product as it would normally be produced.

An advantage to the use of transfected primary or secondary cells of the present invention is that by controlling the number of cells introduced into an individual, one can control the amount of the product delivered to the body. In addition, in some cases, it is possible to remove the transfected cells if there is no longer a need for the product. A further advantage of treatment by use of transfected primary or secondary cells of the present invention is that production of the therapeutic product can be regulated, such as through the administration of zinc, steroids or an agent which affects transcription of a protein, product or nucleic acid product or affects the stability of a nucleic acid product.

The present invention will now be illustrated by the following examples, which are not intended to be limiting in any way.

EXAMPLES

Example 1

Isolation of Fibroblasts a. Source of Fibroblasts.

Human fibroblasts can be obtained from a variety of tissues, including biopsy specimens derived from liver, kidney, lung and skin. The procedures presented here are optimized for the isolation of skin fibroblasts, which are readily obtained from individuals of any age with minimal discomfort and risk (embryonic and fetal fibro-blasts may be isolated using this protocol as well). Minor modifications to the protocol can be made if the isolation of fibroblasts from other tissues is desired.

Human skin is obtained following circumcision or punch biopsy. The specimen consists of three major components: the epidermal and dermal layers of the skin itself, and a fascial layer that adheres to the dermal layer. Fibroblasts can be isolated from either the dermal or fascial layers.

b. Isolation of Human Fascial Fibroblasts.

Approximately 3 $cm^2$ tissue is placed into approximately 10 ml of wash solution (Hank's Balanced Salt Solution containing 100 units/ml penicillin G, 100 $\mu$g/ml streptomycin sulfate, and 0.5 $\mu$g/ml Fungisone) and subjected to gentle agitation for a total of three 10-minute washes at room temperature. The tissue is then transferred to a 100 mm tissue culture dish containing 10 ml digestion solution (wash solution containing 0.1 units/ml collagenase A, 2.4 units/ml grade II Dispase).

Under a dissecting microscope, the skin is adjusted such that the epidermis is facing down. The fascial tissue is separated from the dermal and epidermal tissue by blunt dissection. The fascial tissue is then cut into small fragments (less than 1 $mm^2$) and incubated on a rotating platform for 30 min at 37° C. The enzyme/cell suspension is removed and saved, an additional 10 cc of digestion solution is added to the remaining fragments of tissue, and the tissue is reincubated for 30 min at 37° C.. The enzyme/cell suspensions are pooled, passed through a 15-gauge needle several times, and passed through a Cellector Sieve (Sigma) fitted with a 150-mesh screen. The cell suspension is centrifuged at 1100 rpm for 15 min at room temperature. The supernatant is aspirated and the disaggregated cells resuspended in 10 ml of nutrient medium (see below). Fibroblast cultures are initiated on tissue culture treated flasks (Corning) at a density of approximately 40,000 cells/$cm^2$.

c. Isolation of Human Dermal Fibroblasts. Fascia is removed from skin biopsy or circumcision specimen as described above and the skin is cut into small fragments less than 0.5 $cm^2$. The tissue is incubated with 0.25% trypsin for 60 min at 37° C. (alternatively, the tissue can be incubated in trypsin for 18 hrs at 4° C.). Under the dissecting microscope, the dermis and epidermis are separated. Dermal fibroblasts are then isolated as described above for fascial fibroblasts.

d. Isolation of Rabbit Fibroblasts. The procedure is essentially as described above. Skin should be removed from areas that have been shaved and washed with a germicidial solution surgically prepared using accepted procedures.

Example 2

Culturing of Fibroblasts a. Culturing of Human Fibroblasts. When confluent, the primary culture is trypsinized using standard methods and seeded at approximately 10,000 cells/$cm^2$. The cells are cultured at 37° C. in humidified air containing 5% $CO_2$. Human fibroblast nutrient medium (containing DMEM, high glucose with sodium pyruvate, 10–15% calf serum, 20 mM HEPES, 20 mM L-glutamine, 50 units/ml penicillin G, and 10 μg/ml streptomycin sulfate) is changed twice weekly.

b. Culturing of Rabbit Fibroblasts. The cells are trypsinized and cultured as described for human fibroblasts. Rabbit fibroblast nutrient medium consists of a 1:1 solution of MCDB-110 (Sigma) with 20% calf serum and conditioned medium. Conditioned medium is essentially human fibroblast nutrient medium (with 15% calf serum) removed from rabbit fibroblasts grown in mass culture for 2–3 days.

Figure 3:
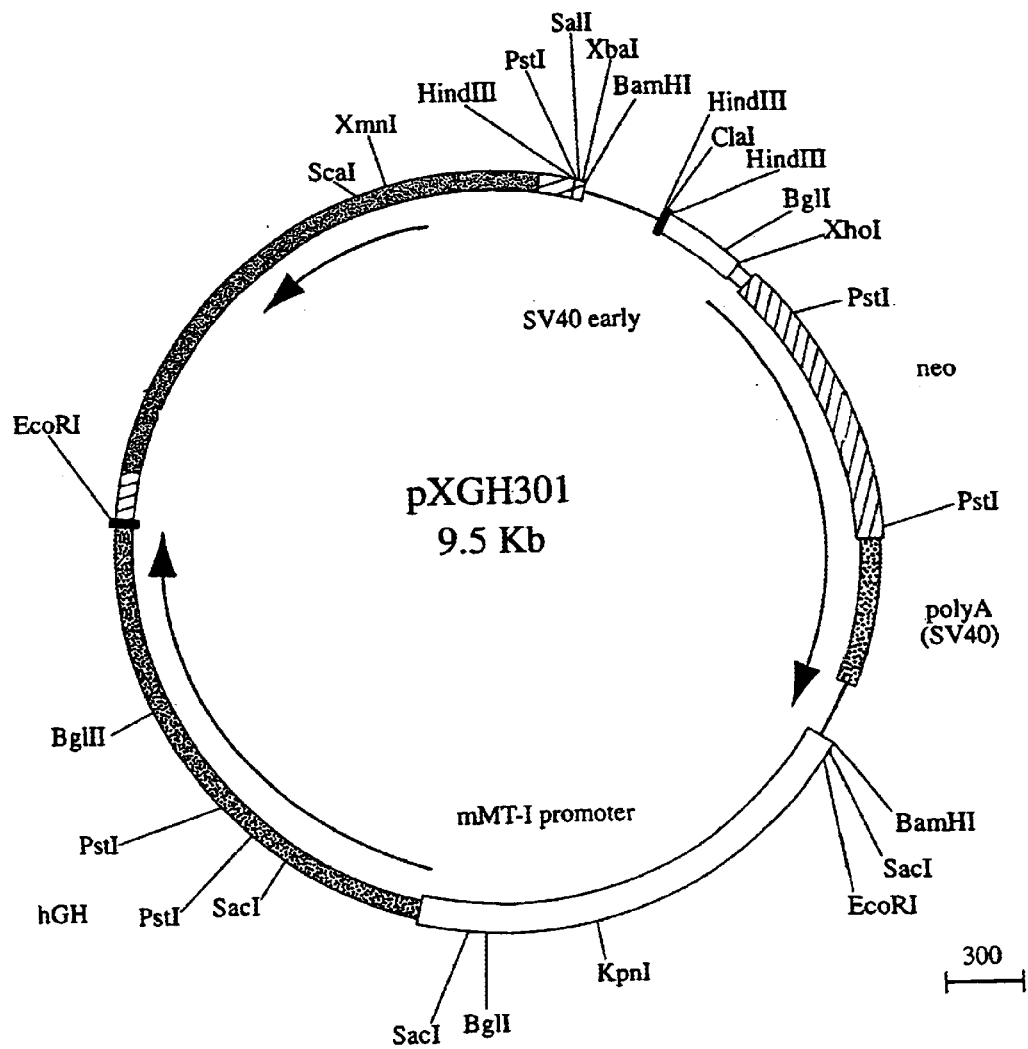
FIG. 3 is a schematic representation of plasmid pXGH301 which includes the human growth hormone gene and the neo gene.

Example 3
Construction of a Plasmid (pXG301) Containing Both the Human Growth Hormone and Neomycin Resistance Genes pXGH301 was constructed by a two-step procedure. The SalI-ClaI fragment from pBR322 (positions 23–651 in pBR322) was isolated and inserted into SalI-ClaI digested pcD NEO, introducing a BamHI site upstream of the SV40 ori region of pcD NEO. This plasmid, pBNEO was digested with BamHI, and the 2.1 kb fragment containing the neo gene under the control of the SV40 early promoter, was isolated and inserted into BamHI digested pXGH5. A plasmid with a single insertion of the 2.1 kb BamHI fragment was isolated in which neo and hGH are transcribed in the same direction relative to each other. This plasmid was designated pXGH301 (FIG. 3).

Example 4
Transfection of Primary and Secondary Fibroblasts with Exogenous DNA and a Selectable Marker Gene by Electroporation Exponentially growing or early stationary phase fibroblasts are trypsinized and rinsed from the plastic surface with nutrient medium. An aliquot of the cell suspension is removed for counting, and the remaining cells are subjected to centrifugation as described above. The supernatant is aspirated and the pellet is resuspended in 5 ml of electroporation buffer (20 mM HEPES pH 7.3, 137 mM NaCl, 5 mM KCl, 0.7 mM $Na_2HPO_4$, 6 mM dextrose). The cells are recentrifuged, the supernatant aspirated, and the cells resuspended in electroporation buffer containing 1 mg/ml acetylated bovine serum albumin. The final cell suspension contains approximately $3 \times 10^6$ cells/ml. Electroporation should be performed immediately following resuspension.

Supercoiled plasmid DNA is added to a sterile cuvette with a 0.4 cm electrode gap (Bio-Rad). The final DNA concentration is generally at least 120 μg/ml. 0.5 ml of the cell suspension (containing approximately $1.5 \times 10^6$ cells) is then added to the cuvette, and the cell suspension and DNA solutions are gently mixed. Electroporation is performed with a Gene-Pulser apparatus (Bio-Rad). Capacitance and voltage are set at 960 μF and 250–300 V, respectively. As voltage increases, cell survival decreases, but the percentage of surviving cells that stably incorporate the introduced DNA into their genome increases dramatically. Given these parameters, a pulse time of approximately 14–20 mSec should be observed.

Electroporated cells are maintained at room temperature for approximately 5 min, and the contents of the cuvette are then gently removed with a sterile transfer pipette. The cells are added directly to 10 ml of prewarmed nutrient media (as above with 15% calf serum) in a 10 cm dish and incubated as described above. The following day, the media is aspirated and replaced with 10 ml of fresh media and incubated for a further 16–24 hrs. Subculture of cells to determine cloning efficiency and to select for G418-resistant colonies is performed the following day. Cells are trypsinized, counted and plated; typically, fibroblasts are plated at $10^3$ cells/10 cm dish for the determination of cloning efficiency and at $1–2 \times 10^4$ cells/10 cm dish for G418 selection.

Human fibroblasts are selected for G418 resistance in medium consisting of 300–400 μg/ml G418 (Geneticin, disulfate salt with a potency of approximately 50%; Gibco) in fibroblasts nutrient media (with 15% calf serum). Cloning efficiency is determined in the absence of G418. The plated cells are incubated for 12–14 days, at which time colonies are fixed with formalin, stained with crystal violet and counted (for cloning efficiency plates) or isolated using cloning cylinders (for G418 plates). Electroporation and selection of rabbit fibroblasts is performed essentially as described for human fibroblasts, with the exception of the nutrient media used. Rabbit fibroblasts are selected for G418 resistance in medium containing 1 gm/ml G418.

Fibroblasts were isolated from freshly excised human foreskins. Cultures were seeded at 50,000 cells/cm in DMEM+10% calf serum. When cultures became confluent fibroblasts were harvested by trypsinization and transfected by electroporation. Electroporation conditions were evaluated by transfection with the plasmid pcDNEO. A representative electroporation experiment using near optimal conditions (60 μg of plasmid pcDNEO at an electroporation voltage of 250 volts and a capacitance setting of 960 μFarads) resulted in one G418 coloney per 588 treated cells (0.17% of all cells treated), or one $G418^r$ colony per 71 clonable cells (1.4%).

When nine separate electroporation experiments at near optimal conditions (60 μg of plasmid pcDneo at an electroporation voltage of 300 volts and a capacitance setting of 960 μFarads) were performed, an average of one $G418^r$ colony per 1,899 treated cells (0.05%) was observed, with a range of 1/882 to 1/7,500 treated cells. This corresponds to an average of one $G418^r$ colony per 38 clonable cells (2.6%).

Low passage primary human fibroblasts were converted to hGH expressing cells by co-transfection with plasmids pcDNEO and pXGH5. Typically, 60 μg of an equimolar mixture of the two plasmids were transfected at near optimal conditions (electroporation voltage of 300 volts and a capacitance setting of 960 μFarads). The results of such an experiment resulted in one $G418^r$ colony per 14,705 treated cells. hGH expression data for these and other cells isolated under identical transfection conditions are summarized below. Ultimately, 98% of all $G418^r$ colonies could be expanded to generate mass cultures.

| | |
|---|---|
| Number of $G418^r$ Clones Analyzed | 154 |
| Number of $G418^r$/hGH Expressing Clones | 65 |
| Average hGH Expression Level | 2.3 μg $hGH/10^6$ Cells/24 hr |
| Maximum hGH Expression Level | 23.0 μg $hGH/10^6$ Cells/24 hr |

Stable transfectants also have been generated by electroporation of primary or secondary human fibroblasts with pXGH301, a DNA construct in which the neo and hGH genes are present on the same plasmid molecule (Example 3). For example, $1.5 \times 10^6$ cells were electroporated with 60 μg pXGH301 at 300 volts and 960 μFarads. G418 resistant colonies were isolated from transfected secondary fibroblasts at a frequency of 652 G418 resistant colonies per $1.5 \times 10^6$ treated cells (1 per 2299 treated cells). Approximately 59% of these colonies express hGH.

Example 5
Isolation of Transfectants in the Absence of Selection

Stable transfection of primary fibroblasts with the plasmid pXGH5 renders recipient fibroblasts capable of secreting human growth hormone (hGH) into the surrounding medium. Therefore, a radioimmunoassay for hGH (or for any expressed protein) can be used as a simple and rapid screen for transfectants as an alternative to the use of selective markers and selective agents. In addition, it should be possible to determine the true frequency of stable integration of exogenous DNA using a screening method such as PCR which does not necessarily rely on gene expression.

The results of experiments to be discussed below demonstrated that it was indeed possible to isolate transfectants stably expressing hGH without selection of a cotransfected plasmid. These experiments have been successful for primary human foreskin fibroblasts and primary rabbit skin fibroblasts. The frequency of stably expressing transfectants was approximately 1 in 10 colonies.

1. Human Foreskin Tissue

Approximately $2.0 \times 10^6$ human cells that were freshly dissociated from tissue were electroporated with 60 μg of pXGH5 at 300 volts, 960 μFarads. The cells were plated immediately in a 100 mm tissue culture dish containing 10 ml of prewarmed medium and incubated at 37° C. in a humidified 5% $CO_2$ atmosphere. Two days following transfection, $5 \times 10^3$ cells were subcultured into a 24 well cloning plate (Bellco Glass Co.). Each well of the 24 well plate contained 16 smaller wells (384 wells/plate). Eight days later 10 of 24 large wells were screened for hGH expression via radioimmune assay. All ten wells exhibited significant hGH expression. The media was aspirated, replaced with fresh media and assayed for hGH 24 hours later. Again all ten wells were expressing significant levels of hGH. Colony counts were performed for each of the ten wells at this time. An average of 11.5 colonies per large well was observed. If one assumes a minimum of one stable transfectant per well, a lower limit frequency of transfection of approximately 8–9% of clonable cells can be calculated.

Individual colonies in each of the 16 small wells within one of these larger wells were trypsinized and transferred to 16 wells of a 96 well plate. Three days later each of these wells was assayed for hGH expression. One of the 16 was found to contain cells expressing hGH. The cells in this well were expanded in culture. These cells, HF26-19M, were producing 260 ng hGH/$10^6$ cells/24 hr after 42 mpd in culture.

The above experiment was repeated using another primary human foreskin fibroblast culture. From this experiment a second clone expressing hGH was isolated. After 24 mpd in culture these cells, HF24-GH1, were producing 60 ng hGH/$10^6$ cells/24 hr. hGH production continued until the cells reached 45 mpd, at which point the cells were frozen away. The lower limit transfection frequency was similar to the first experiment (6–7% of clonable cells).

2. Primary Rabbit Fibroblasts

Primary rabbit skin cells were transfected with pXGH5. The electroporation conditions were identical to the human tissue electroporation described above. $1 \times 10^3$ cells were subcultured into a 384 well plate. Seven days later, hGH assays were performed for 10 of the 24 larger wells. Nine of the ten wells were expressing hGH. One of these wells was chosen for colony isolation. This well contained nine colonies dispersed among the 16 small wells. Cells in each of the 16 small wells were trypsinized and transferred to 16 wells of a 96 well plate. Subsequent hGH assays showed that one of these 16 wells was expressing hGH. This clone was expanded in culture. hGH production was at 58 ng/$10^6$ cells/24 hr after 35 mpd in culture. The estimated transfection frequency for this experiment was 1 colony expressing hGH out of nine total colonies (11%).

Example 6
Stable Transfection of Primary Human Fibroblasts by Microinjection Direct injection of DNA into cell nuclei is another method for stably transfecting cells. The ability of primary and secondary human foreskin fibroblasts to be stably transfected by this method has not been previously reported. The 8 kb HindIII fragment from plasmid RV6.9h (Zheng, H. et al., *Proc. Natl. Acad. Sci. USA* 88:18 8067–8071 (1991)) was purified by gel electrophoresis and passage through an anion exchange column (QIAGEN Inc.). DNA at (10 μg/ml) was injected into primary or secondary human foreskin fibroblasts using 0.1 μm outer diameter glass needles. 41 $G418^r$ clones were isolated after injection of 2,000 cells (1 in 49 starting cells). hGH expressing clones were also generated by micro-injection. Plasmid pXGH301 was linearized by ScaI digestion (which cuts once within the $amp^r$ gene in the pUC12 backbone), purified by passage through an anion exchange column (QIAGEN Inc.), and injected into secondary human foreskin fibroblasts using 0.1 μm outer diameter glass needles. Several DNA concentrations were used, ranging from 2.5–20 μg pXGH301/ml. Twenty G418 resistant clones were isolated after microinjection into 2,100 cells (1 in 105 starting cells). The fraction of $G418^r$ cells, is approximately 1% of all cells treated. Nine of 10 clones analyzed were expressing hGH, with average hGH expression being 0.6 μg/$10^6$ cells/24 hr for clones isolated in this experiment, and 3 clones were expanded for studying long-term expression of hGH. All 3 were expressing hGH stably, with hGH still being produced through 33, 44, and 73 mpd for the 3 strains, respectively.

Figure 5:
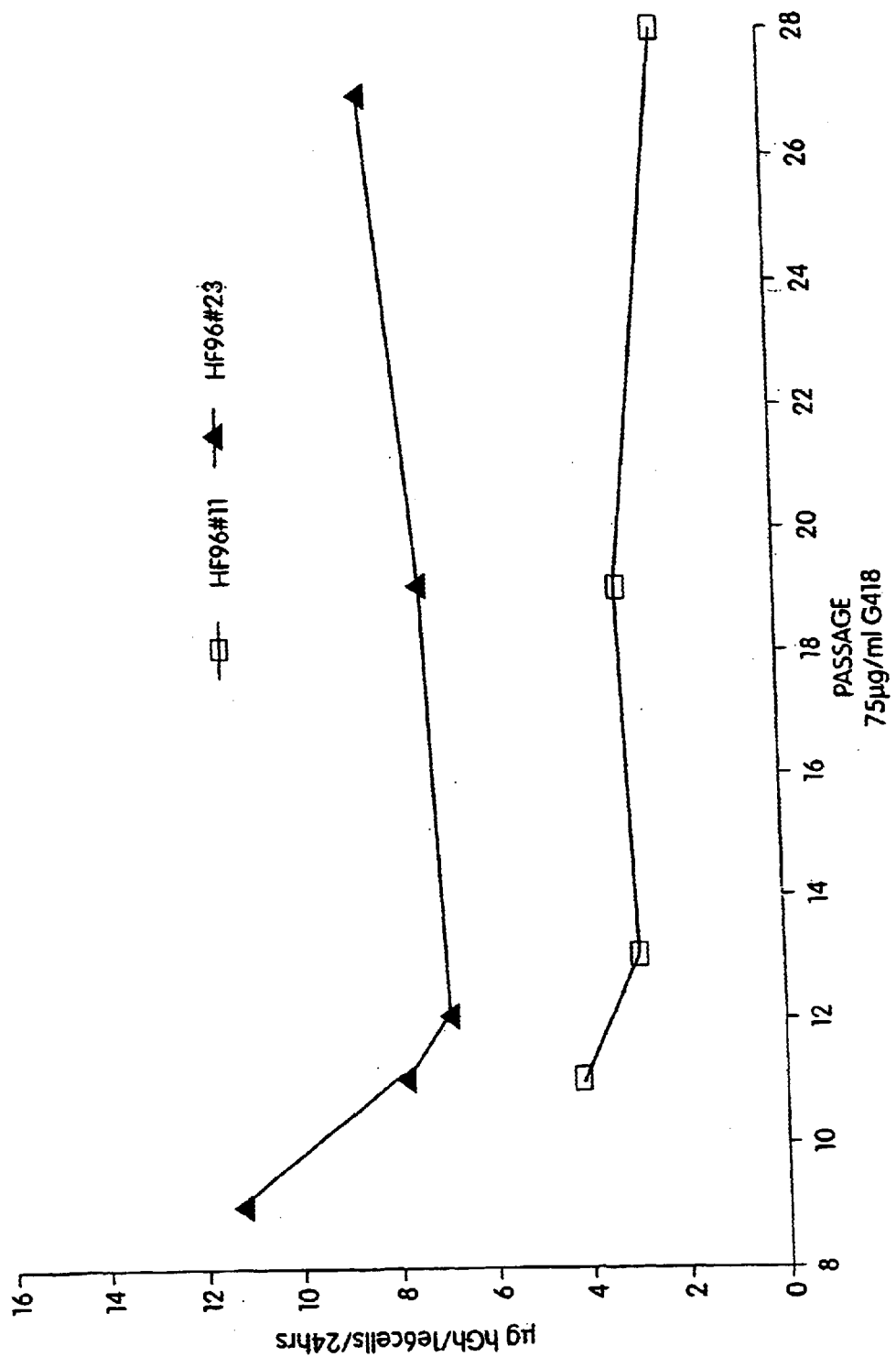
FIG. 5 shows results of an assessment of long-term in vitro hGH production by transfected primary human skin fibroblasts (two strains, HF96-11 and HF96-23).

Example 7
Long Term in vitro hGH Production by Cell Strains Derived from Transfected Primary Human Skin Fibroblasts Fibroblasts were isolated from freshly excised human skin fibroblasts and cultured in DMEM+10% calf serum. Electroporation (250 volts, 960 μFarads) with 60 μg of an equimolar mixture of pcDNEO and pXCH5 was performed and treated cells were selected in G418-containing medium (300 μg/ml C418). Colonies were isolated and expanded using standard methods, and the resulting primary cell strains were subcultured repeatedly in order to monitor the stability of hCH expression as a function of time in culture. Data derived from two such strains, HF96-11 and HF96-23, is shown in FIG. 5. Cells were maintained in a low level of G418 (75 μ/ml C418) in DMEM+10% calf serum and subcultured at a seeding density of 10,000 cells/$cm^2$. Culture medium was changed 24 hr prior to harvesting the cells for passaging. At the time of passage an aliquot of the culture medium was removed for hGH assay and the cells were then harvested, counted, and reseeded. hGH concentration in the medium was determined using a commercially available immunoassay. hGH levels (expressed as μg hGH/$10^6$ cells/24 hr) are plotted for various culture passage numbers from 9 to 28 passages. hGH expression remains remarkably constant throughout this extended in vitro culture interval (HF96-11 at passage 28 reached 69 mpd, while HF96-23 at passage 27 reached 76 mpd).

Figure 6:
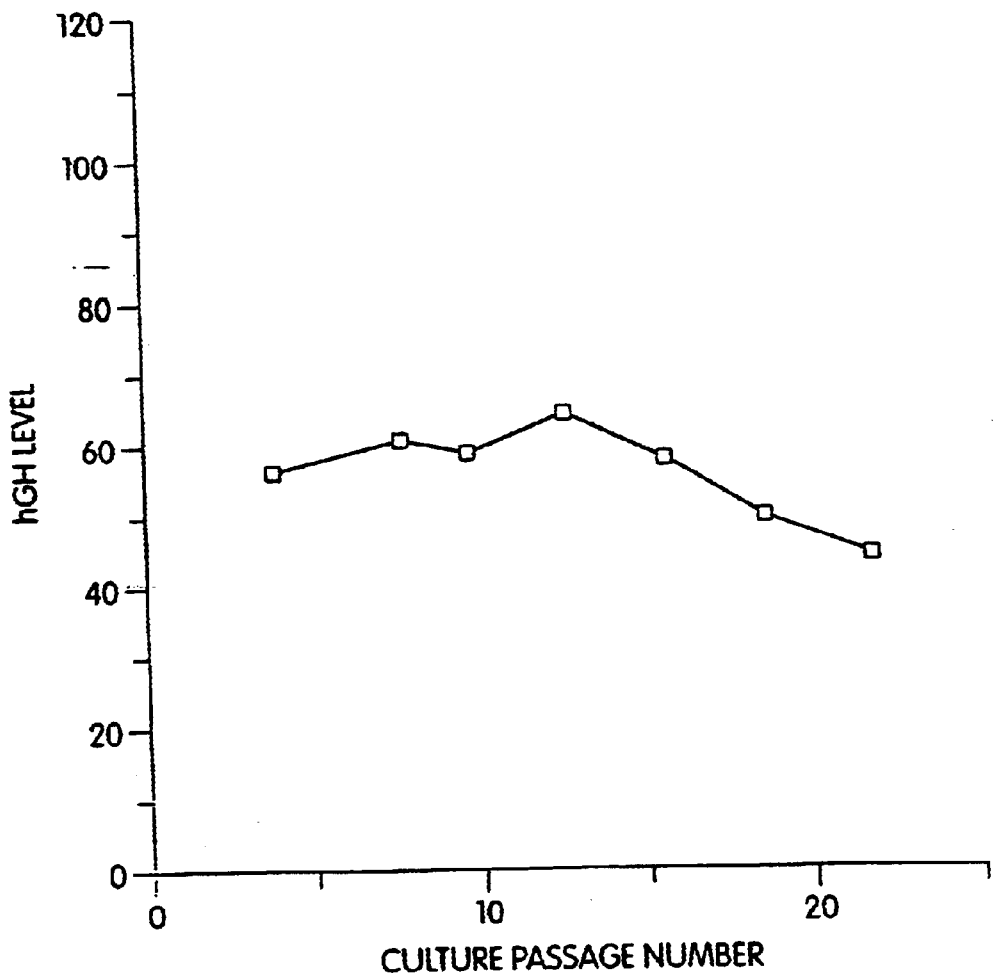
FIG. 6 is a graphic representation of human growth hormone (hGH) expression by transfected primary rabbit skin fibroblasts in vitro.

Example 8
Long Term In vitro hGH Production by Cell Strains Derived from Transfected Primary and Secondary Rabbit Skin Fibroblasts Fibroblasts were isolated from freshly excised rabbit skin and cultured in DMEM+10% calf serum. Electroporation (250 volts, 960 µFarads) with 60 µg of an equimolar mixture of pcD NEO and pXGH5 was performed and treated cells were selected in C418-containing medium (1 mg/ml G418). Colonies were isolated using cloning cylinders and expanded using standard methods, and the resulting primary cell strains were subcultured repeatedly in order to monitor the stability of hGH expression as a function of time in culture. Data derived from one such strain, RF40/1–3 is shown in FIG. 6. RF40/1–3 cells were maintained in the absence of selection in rabbit fibroblast nutrient medium and sub-cultured at a seeding density of 10,000 cells/cm$^2$. Culture medium was changed 24 hr prior to harvesting the cells for passaging. At the time of passage an aliquot of the culture medium was removed for hGH assay and the cells were then harvested, counted, and reseeded. hGH concentration in the medium was determined using a commercially available immunoassay. (Nichols Institute) hGH levels (expressed as µg hGH/10$^6$ cells/24 hr) are plotted for culture passage numbers, 4, 8, 10, 13, 16, 19, and 22, corresponding to culture mean population doubling (mpd) levels of approximately 28 through 84. hGH expression remains remarkably constant throughout this extended in vitro culture interval and virtually identical to the levels observed at approximately 20 mpd in culture (47 µg hGH/10$^6$ cells/24 hr).

Example 9
Long-term Expression of Human Growth Hormone in Mice

The nude mouse provides a valuable system to study implants of genetically engineered cells for their ability to deliver therapeutically useful proteins to an animal's general circulation. The relative immune-incompetence of these animals may allow certain primary and secondary rabbit fibroblasts to survive in vivo for extended periods.

For implantation of cells into the subrenal capsule, mice are given intraperitoneal injection of Avertin (a solution of 2% w/v 2.2.2 tribromoethanol and 2% v/v 2-methyl, 2-butanol.) at a dose of 0.017 ml/g body weight. The kidney (generally the left kidney) is approached through an 8–10 mm incision made approximately 3 mm below the rib cage. The skin, abdominal musculature, peritoneum, and perirenal fascia are retracted to expose the kidney. A small forcep is used to pull the kidney out of the abdominal cavity. A 27-gauge hypodermic needle is used to make a small opening in the renal capsule. Using a 20-gauge I.V. catheter, cells to be implanted (typically 3 million cells in a volume of 5–10 µl) are withdrawn into a I ml syringe and slowly ejected under the renal capsule. Care is taken to ensure that the cells are released distal to the opening in the renal capsule. The incision is closed with one staple through the musculature and the skin. Blood is collected after placing the mouse in a large beaker containing methoxyflurane until light anesthesia is achieved. The tip of a Pasteur pipette is placed between the eye and the periorbital space to collect blood from the orbital sinus. Serum hGH levels are determined using a commercially available kit (Nichol's Institute).

In our initial experiment, a nude mouse was implanted with 5 million transfected rabbit fibroblast cells (strain RF20-11). This mouse has displayed detectable hGH in its serum for one year. The time course of expression is shown below.

| Month | 1 | 2 | 3 | 4 | 6 | 12 |
|---|---|---|---|---|---|---|
| Serum hGH (ng/ml): | 0.7 | 0.7 | 0.8 | 0.6 | 0.7 | 0.6 |

Data from a larger experiment in which animals were implanted with a rabbit fibroblast strain (RF40/1-3) expressing 96 µg/10$^6$ cells/24 hr is presented in FIG. 7. Average serum hGH levels have remained relatively constant for over 11 months, averaging from 1–3 ng/ml since implantation. No side effects of any type arising from the implanted cells have been observed over this time period.

Example 10
Reculturing hGH Producing Cells from Subrenal Capsule Implants

Figure 8A:
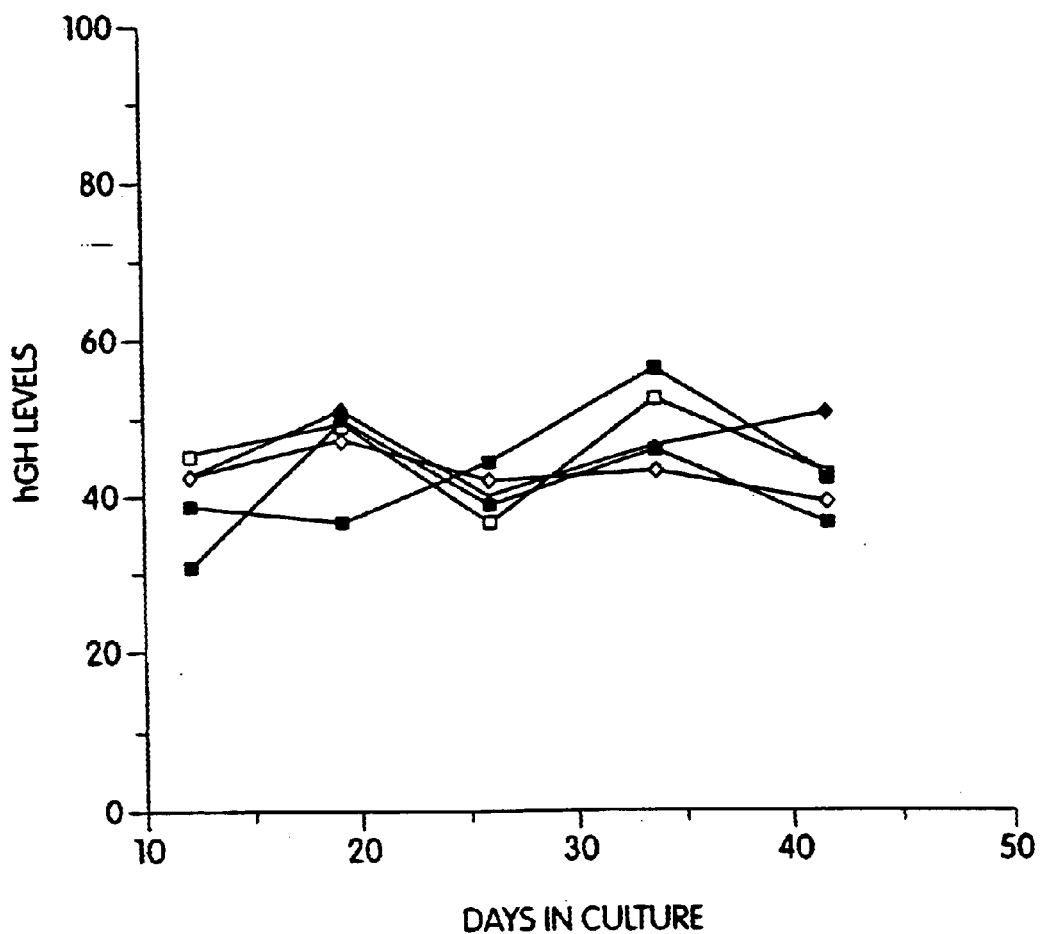
FIGS. 8A and 8B shows graphic representations of recultured implants from mice which had subrenal capsule implants of fibroblasts expressing hGH.
Figure 8B:
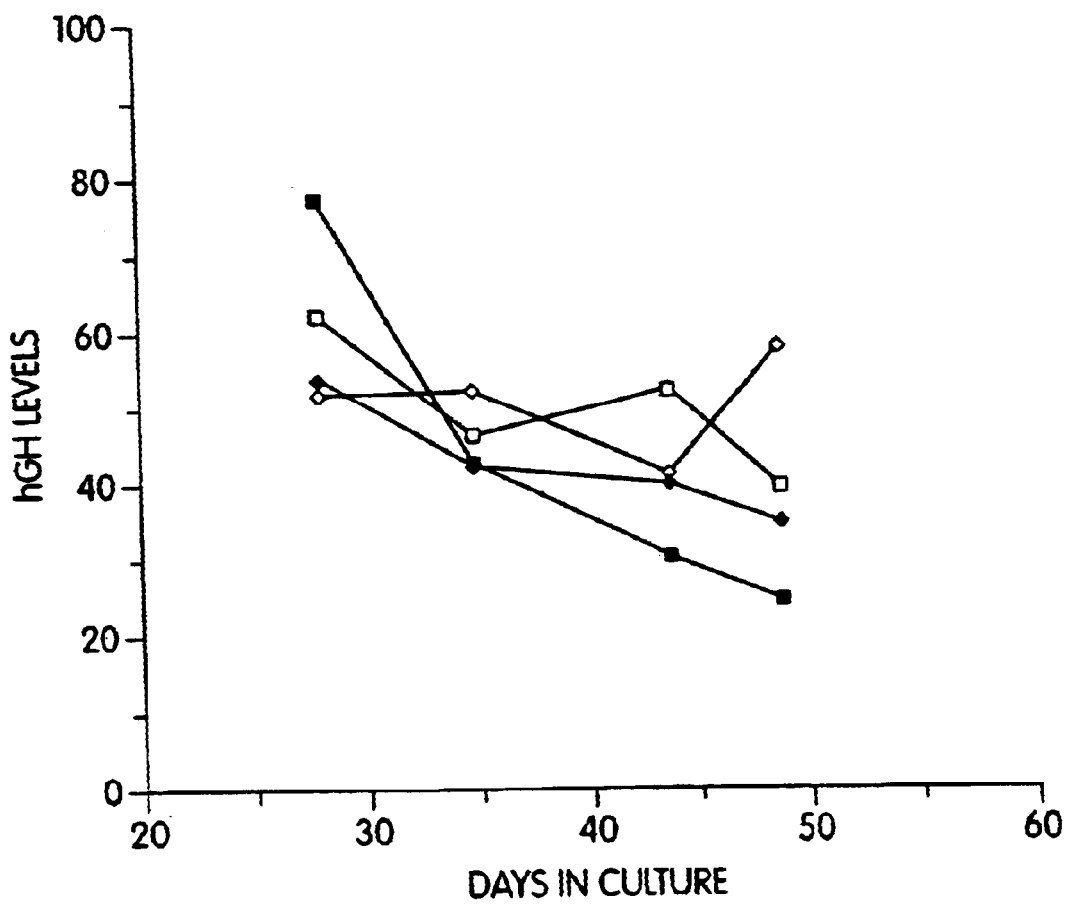

A stringent test of the viability of implanted cells is their ability to grow and display their preimplantation properties when removed from animals and recultured in vitro. RF40/1-3 cells (3×10$^6$ cells per mouse) expressing 24.5 µg hGH/10$^6$ cells/24 hr were implanted under the subrenal capsule of nude mice. These cells had undergone 49 mpd in culture prior to implantation. After either 5 or 10 weeks in vivo, the animals were sacrificed, kidneys were harvested, and cells in the vicinity of the implant (clearly visible on the surface of the kidney) were microdissected out. The resulting tissue was subjected to a scaled-down version of a standard enzymatic cell dispersion protocol (Example 3), and the single cell suspension was placed in G418-containing medium. Cell culture data on 5 recultured implants from mice having 5-week-old implants, and 4 recultured implants from mice having 10-week-old implants, are shown in FIGS. 8A and 8B, respectively. hGH levels (expressed as µg hGH/10$^6$ cells/24 hr) are reported for various times after placing the cells in culture. In FIGS. 8A and 8B, the recovered cells were propagated for 19 mpd in culture. In both cases, G418$^r$ cells expressing high levels of hGH were recovered, with hGH expression being relatively stable over the 19 in vitro population doublings post-recovery.

Example 11
Expression of Human Growth Hormone and Production of High Titer Anti-hGH Anti-Sera in Rabbits Implanted with Transfected Autologous Cells An experiment that explores all of the technical and logistical requirements for performing autologous gene therapy was performed in rabbits. First, skin biopsies were taken from 8 living rabbits. Skin fibroblasts were isolated and placed in primary culture. After one passage in vitro, cells were transfected with either pXGH301 or cotransfected with pXGH5 and pcDNEO. G418 resistant clones were isolated and analyzed for hGH expression. Clones expressing greater than 10 µg/10$^6$ cells/day were expanded into roller bottles. Finally, cells from each clone were harvested from roller bottles and prepared for either SRC implantation or IP injection into the same rabbit used as the donor for the skin biopsy.

To isolate rabbit skin fibroblasts, the rabbit is anesthetized with an intramuscular injection of Ketamine-HCl (50 mg/kg body weight) and Xylazine-HCl (5 mg/kg body weight) until sedation is achieved. The animal is shaved in the area, for example, above the right pelvic joint and prepped for surgery using accepted procedures. Two arc-shaped incisions are made approximately 3 cm apart which are joined at the dorsal and ventral areas to form an oval-shaped patch. A serrated forcep is used to remove the epidermis and a small scissor is used to remove the underlying fascia. The dermis and fascia are placed in culture medium and the incision is closed with a 3-0 nylon suture. Rabbits are placed on a heating pad for recovery. Fascial fibroblasts are cultured, transfected, and selected as described in Example 1, 2, and 4.

For implantation of cells into the renal capsule, the rabbits are anesthetized as described above. The animal is placed in a right side lateral recumbent position exposing the area below the left rib cage. The animal is shaved and prepped according to accepted procedures. The left kidney is approached through a 6 cm dorso-ventral incision approximately 2 cm below the twelfth rib. The incision is carried through the abdominal musculature, peritoneum, and peri-renal fat and fascia. A Balfour retractor is used to maintain the abdominal opening while dissection of peri-renal fat and fascia is performed. Using an 11-gauge surgical blade, a 2–3 mm incision is made at the surface of the renal capsule. Using a 20-gauge I.V. catheter, cells to be implanted (typically 100–200 million cells in a volume of 165–660 μl) are drawn into a 1 ml syringe and slowly ejected under the renal capsule. Care is taken to ensure that the cells are released distal to the opening in the renal capsule. The peritoneal cavity is closed by suturing the peritoneum and abdominal muscle with 3-0 adsorbable chromic gut. The skin is closed with a 3-0 nylon suture and a sterile gauze bandage and antibiotic ointment (Bactrin) is applied to the wound. Rabbits are placed on a heating pad for recovery. Systemic antibiotics (Tribrissin) are administered after skin biopsy and implantation. For introducing cells by the intra-peritoneal (IP) route, cells (700–1100 million in a volume of 3.5–5.5 ml) are injected through a 22-gauge needle. Blood is collected from the middle auricular artery in restrained animals using a 22-gauge needle.

Figure 9:
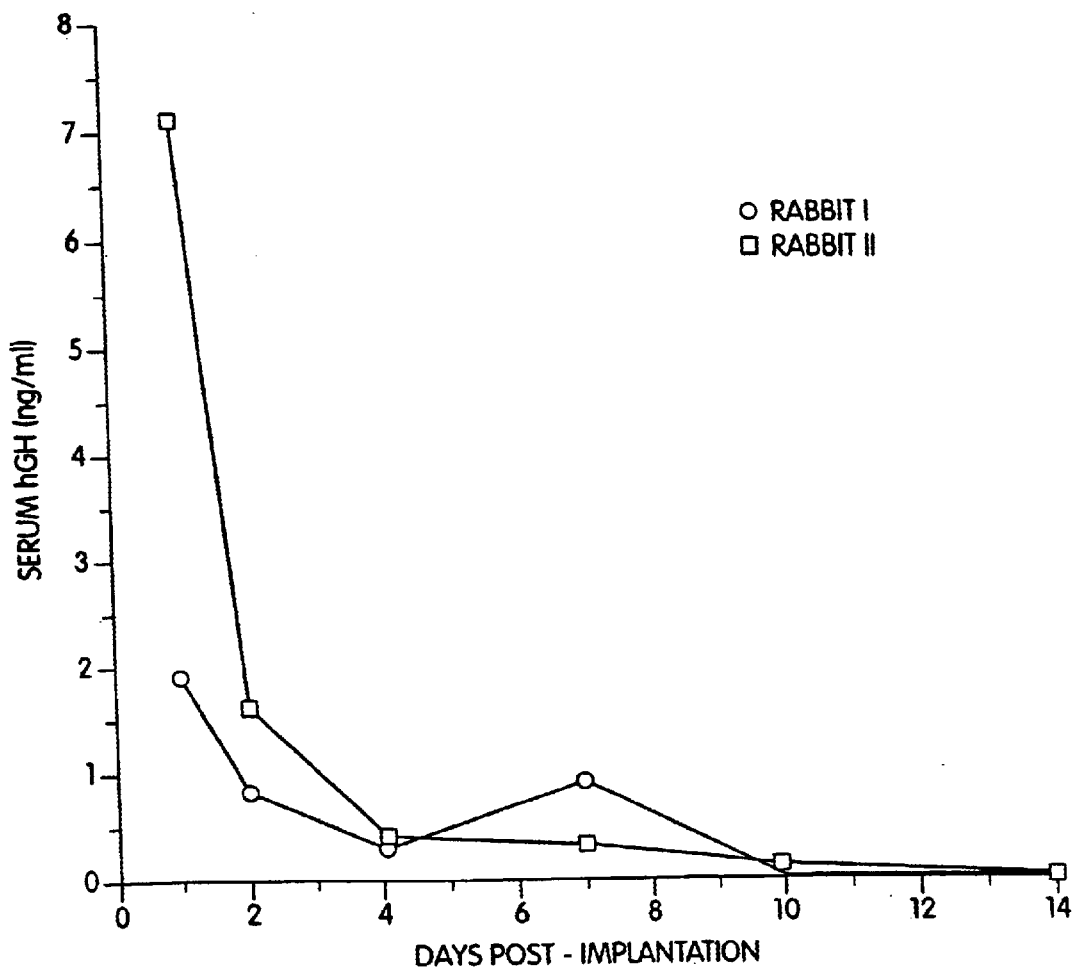
FIG. 9 is a graphic representation of hGH expression over time in rabbits in which cells expressing hGH were implanted under the renal capsule.
Figure 10:
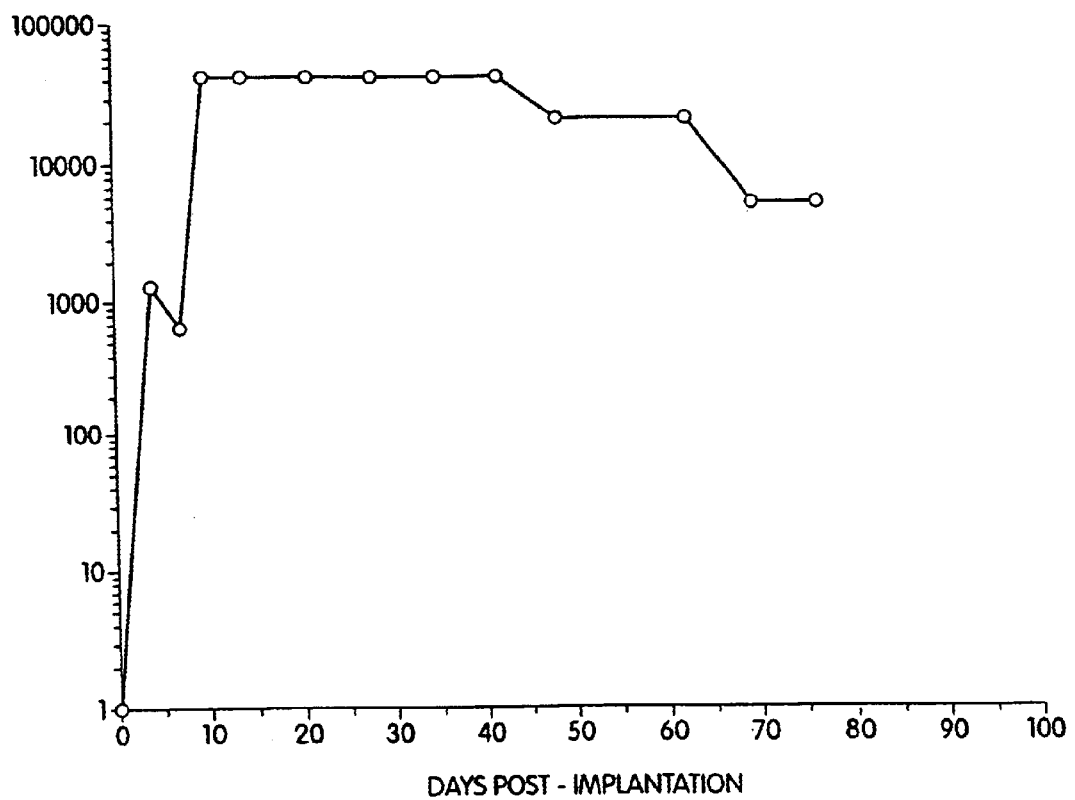
FIG. 10 is a graphic representation of anti-hGH antibody production in a rabbit implanted with hGH expressing cells.

The relevant information on hGH expression levels and numbers of cells introduced into animals is listed in the Table, and this data for two rabbits is shown in FIG. 9. In all eight animals, serum hGH levels were readily detectable. By day 14, no hGH could be detected in any animal. The eventual disappearance of hGH in the serum of these animals was expected, since human growth hormone is known to be antigenic in rabbits. Serum samples were therefore assayed for anti-hGH antibodies (quantified by an anti-rabbit IgG ELISA). The results of this analysis for two of the rabbits that had IP implants are shown in FIG. 10. In each case, the decrease in serum hGH levels coincides with a rise in anti-hGH antibodies.

These results indicate that there appears to be no technical barrier to performing autologous gene therapy in rabbits using transfected skin fibroblasts. hGH delivery by genetically engineered autologous cells was successful in all 8 experimental animals. As expected, serum hGH levels decreased concomitantly with a rise in anti-hGH antibodies. High titers (1:40,000) were not uncommon in animals with IP or SRC implants, consistent with the proposal that continuous delivery of proteins by a single implantation treatment can be an efficient method for vertebrate vaccination and the production of high titer antisera against protein antigens.

TABLE

Autologous Implantation Of hGH Expressing Fibroblasts Into Rabbits

| Experiment/ Rabbit | # Cells (×10E6) | Implant Site | In Vitro Expression |
|---|---|---|---|
| TKR5 | 120 | SRC | 14.0 |
| TKR6 | 160 | SRC | 9.9 |
| TKR10 | 120 | SRC | 8.0 |
| TKR13 | 127 | SRC | 2.8 |
| TKR9 | 900 | IP | 8.0 |
| TKR11 | 1089 | IP | 0.7 |
| TKR12 | 840 | IP | 3.6 |
| TKR14 | 726 | IP | 6.7 |

| Experiment/ Rabbit | SERUM hGH (ng/ml) | | | | | |
|---|---|---|---|---|---|---|
| | 1 day | 2 day | 4 day | 7 day | 10 day | 14 day |
| TKR5 | 1.9 | 0.8 | 0.3 | 0.9 | <0.1 | <0.1 |
| TKR6 | 7.4 | 3.1 | 0.7 | 0.6 | 0.2 | <0.1 |
| TKR10 | 4.7 | 1.4 | 0.3 | <0.1 | <0.1 | <0.1 |
| TKR13 | 0.6 | 0.6 | 0.2 | 0.2 | 0.5 | <0.1 |
| TKR9 | 34.5 | 3.4 | 0.9 | 0.8 | <0.1 | <0.1 |
| TKR11 | 3.6 | 0.3 | 0.2 | 0.1 | <0.1 | <0.1 |
| TKR12 | 7.1 | 1.6 | 0.4 | 0.3 | 0.1 | <0.1 |
| TKR14 | 95.0 | 28.3 | 6.3 | <0.1 | <0.1 | <0.1 |

Example 12

Production of Transfected Cell Strains by Gene Targeting

Gene targeting occurs when transfecting DNA either integrates into or partially replaces chromosomal DNA sequences through a homologous recombinant event. While such events may occur in the course of any given transfection experiment, they are usually masked by a vast excess of events in which plasmid DNA integrates by non-homologous, or illegitimate, recombination.

One approach to selecting the targeted events is by genetic selection for the loss of a gene function due to the integration of transfecting DNA. The human HPRT locus encodes the enzyme hypoxanthine-phosphoribosyl transferase. hprt-cells can be selected for by growth in medium containing the nucleoside analog 6-thioguanine (6-TG): cells with the wild-type (HPRT+) allele are killed by 6-TG, while cells with mutant (hprt−) alleles can survive. Cells harboring targeted events which disrupt HPRT gene function are therefore selectable in 6-TG medium. The plasmid pE3-neo contains essentially 6.9 kb of DNA surrounding exons 2 and 3 of the human HPRT gene, with the neo gene inserted into a position which disrupts the coding capacity of exon 3. The replacement of the normal HPRT exon 3 with the neo-disrupted version will result in an hprt−, 6-TG resistant phenotype. Such cells will also be G418 resistant. pE3-neo can be digested with HindIII (separates the HPRT-neo fragment from the pUC12 backbone) and transfected into secondary human foreskin fibroblasts. Three million cells in a volume of 0.5 ml are electroporated at 250 volts and 960 Farads, with 100 μg of pE3-neo. Cells are processed and selected for G418 resistance as described in Example 4, except that 500,000 cells per 150 mm culture dish are plated for G418 selection. After 10 days under selection, the culture medium is replaced with human fibroblast nutrient medium containing 400 μg/ml G418 and 10 μM 6-TG. Selection with the two drug combination is continued for 10 additional days. Plates are scanned microscopically to localize human fibroblast colonies resistant to both drugs. The fraction of G418$^r$ 6-TGr colonies is 4 per 9 million treated cells. Colonies resistant to both drugs have also been isolated by transfecting primary cells [1/3.0×10$^7$].

Targeting at the HPRT locus is verified by restriction enzyme and Southern hybridization analysis using HPRT and neo probes.

A variant of pE3-neo, in which a gene of therapeutic interest is inserted within the HPRT coding region, adjacent to or near the neo gene, can be used to target said gene of therapeutic interest to a specific position in a recipient primary or secondary cell genome.

Equivalents

Those skilled in the art will recognize, or be able to ascertain using not more than routine experimentation, many equivalents to the specific embodiments of the invention described herein. Such equivalents are intended to be encompassed by the following claims.

What is claimed is:

1. A method of producing a therapeutic product in a mammal, said method comprising the steps of:
   a) obtaining a source of primary cells from a mammal;
   b) introducing into primary cells obtained in (a) a nucleic acid molecule construct comprising exogenous nucleic acid sequences encoding a therapeutic product and nucleic acid sequences that direct expression of the exogenous nucleic acid sequences in primary cells, thereby producing primary cells that express the exogenous nucleic acid sequences encoding the therapeutic product;
   c) culturing a primary cell that expresses the exogenous nucleic acid sequences encoding the therapeutic product produced in (b) to produce a clonal cell strain of secondary cells from the primary cell; and
   d) introducing secondary cells produced in (c) into a mammal to produce the therapeutic product in the mammal.

2. The method of claim 1, wherein the primary cells are selected from the group consisting of fibroblasts, keratinocytes, epithelial cells, endothelial cells, glial cells, neural cells, blood cells, hepatocytes, and precursors thereof.

3. The method of claim 1, wherein the therapeutic product is selected from the group consisting of enzymes, cytokines, hormones, antigens, antibodies, clotting factors, regulatory proteins, ribozymes, transcription proteins, receptors, and anti-sense nucleic acid molecules.

4. A method of producing a therapeutic product in a mammal, said method comprising the steps of:
   a) obtaining a source of primary cells from a mammal;
   b) producing a population of secondary cells from primary cells obtained in (a);
   c) introducing into secondary cells produced in (b) a nucleic acid molecule construct comprising exogenous nucleic acid sequences encoding a therapeutic product and nucleic acid sequences that direct expression of the exogenous nucleic acid sequences in secondary cells, thereby producing secondary cells that express the exogenous nucleic acid sequences encoding the therapeutic product;
   d) culturing a secondary cell that expresses the exogenous nucleic acid sequences encoding the therapeutic product produced in (c) to produce a clonal cell strain of secondary cells from the secondary cell; and
   e) introducing secondary cells produced in (d) into a mammal to produce the therapeutic product in the mammal.

5. The method of claim 4, wherein the primary cells are selected from the group consisting of fibroblasts, keratinocytes, epithelial cells, endothelial cells, glial cells, neural cells, blood cells, hepatocytes, and precursors thereof.

6. The method of claim 4, wherein the therapeutic product is selected from the group consisting of enzymes, cytokines, hormones, antigens, antibodies, clotting factors, regulatory proteins, ribozymes, transcription proteins, receptors, and anti-sense nucleic acid molecules.

7. A method of producing a therapeutic product in a mammal, said method comprising the steps of:
   a) obtaining a source of primary cells from a mammal;
   b) introducing into primary cells obtained in (a) a nucleic acid molecule construct comprising exogenous nucleic acid sequences encoding a therapeutic product and nucleic acid sequences that direct expression of the exogenous nucleic acid sequences in primary cells, thereby producing a mixture of primary cells that includes primary cells that express the exogenous nucleic acid sequences encoding the therapeutic product;
   c) culturing a mixture of primary cells produced in (b) to produce a heterogenous cell strain of secondary cells that express the exogenous nucleic acid sequences encoding the therapeutic product; and
   d) introducing secondary cells produced in (c) into a mammal to produce the therapeutic product in the mammal.

8. The method of claim 7, wherein the primary cells are selected from the group consisting of fibroblasts, keratinocytes, epithelial cells, endothelial cells, glial cells, neural cells, blood cells, hepatocytes, and precursors thereof.

9. The method of claim 7, wherein the therapeutic product is selected from the group consisting of enzymes, cytokines, hormones, antigens, antibodies, clotting factors, regulatory proteins, ribozymes, transcription proteins, receptors, and anti-sense nucleic acid molecules.

10. A method of producing a therapeutic product in a mammal, said method comprising the steps of:
    a) obtaining a source of primary cells from a mammal;
    b) producing a population of secondary cells from primary cells obtained in (a);
    c) introducing into secondary cells produced in (b) a nucleic acid molecule construct comprising exogenous nucleic acid sequences encoding a therapeutic product and nucleic acid sequences that direct expression of the exogenous nucleic acid sequences in secondary cells, thereby producing a mixture of secondary cells that includes secondary cells that express the exogenous nucleic acid sequences encoding the therapeutic product;
    d) culturing a mixture of secondary cells produced in (c) to produce a heterogenous cell strain of secondary cells that express the exogenous nucleic acid sequences encoding the therapeutic product; and
    e) introducing secondary cells produced in (d) into a mammal to produce the therapeutic product in the mammal.

11. The method of claim 10, wherein the primary cells are selected from the group consisting of fibroblasts, keratinocytes, epithelial cells, endothelial cells, glial cells, neural cells, blood cells, hepatocytes, and precursors thereof.

12. The method of claim 10, wherein the therapeutic product is selected from the group consisting of enzymes, cytokines, hormones, antigens, antibodies, clotting factors, regulatory proteins, ribozymes, transcription proteins, receptors, and anti-sense nucleic acid molecules.

13. A method of producing a protein in a mammal at physiologically relevant levels, said method comprising administering to the mammal transfected primary cells of mammalian origin that express the protein in sufficient quantity to produce physiologically relevant levels of the protein in the mammal.

14. The method of claim 13, wherein the transfected primary cells are human cells.

* * * * *

UNITED STATES PATENT AND TRADEMARK OFFICE
CERTIFICATE OF CORRECTION

PATENT NO.    : 6,692,737 B1
DATED         : February 17, 2004
INVENTOR(S)   : Selden et al.

It is certified that error appears in the above-identified patent and that said Letters Patent is hereby corrected as shown below:

Column 7,
Line 33, "protion (s)" should be -- portion (s) --.

Column 14,
Line 24, "coloney" should be -- colony --.

Signed and Sealed this

Twentieth Day of July, 2004

JON W. DUDAS
*Acting Director of the United States Patent and Trademark Office*